(12) United States Patent
Brenneisen et al.

(10) Patent No.: US 9,585,840 B1
(45) Date of Patent: Mar. 7, 2017

(54) REDOX ACTIVE CERIUM OXIDE NANOPARTICLES AND ASSOCIATED METHODS

(75) Inventors: Peter Brenneisen, Dusseldorf (DE); Sudipta Seal, Orlando, FL (US); Ajay Karakoti, Richland, WA (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 139 days.

(21) Appl. No.: 13/548,795

(22) Filed: Jul. 13, 2012

Related U.S. Application Data

(63) Continuation of application No. 12/834,302, filed on Jul. 12, 2010, now abandoned.

(60) Provisional application No. 61/224,602, filed on Jul. 10, 2009.

(51) Int. Cl.
*A61K 9/14* (2006.01)
*C08K 3/22* (2006.01)

(52) U.S. Cl.
CPC ...... *A61K 9/143* (2013.01); *C08K 2003/2213* (2013.01); *Y10S 977/773* (2013.01); *Y10S 977/911* (2013.01)

(58) Field of Classification Search
None
See application file for complete search history.

(56) References Cited

U.S. PATENT DOCUMENTS

| | | | |
|---|---|---|---|
| 5,089,860 A | 2/1992 | Deppe et al. | |
| 5,411,647 A | 5/1995 | Johnson et al. | |
| 5,486,359 A | 1/1996 | Caplan et al. | |
| 5,910,311 A | 6/1999 | Boussourira | |
| 5,961,993 A | 10/1999 | Boussourira | |
| 6,042,714 A | 3/2000 | Lin et al. | |
| 6,103,247 A | 8/2000 | Boussourira | |
| 6,139,985 A | 10/2000 | Borglum et al. | |
| 6,316,012 B1 | 11/2001 | N'Guyen | |

(Continued)

FOREIGN PATENT DOCUMENTS

| WO | WO 99/15891 | 4/1999 |
|---|---|---|
| WO | WO 03/059263 A2 | 7/2003 |

(Continued)

OTHER PUBLICATIONS

JM Perez, A Asati, S Nath, C Kaittanis. "Synthesis of Biocompatible Dextran-Coated Nanoceria with pH-Dependent Antioxidant Properties." Small, vol. 4 No. 5, 2008, pp. 552-556.*

(Continued)

*Primary Examiner* — Isaac Shomer
(74) *Attorney, Agent, or Firm* — Timothy H. Van Dyke; Beusse, Wolter, Sanks & Maire PLLC

(57) ABSTRACT

Nanoparticles disclosed in the invention comprise a dextran-coated crystalline structure of cerium oxide wherein tetravalent $Ce^{4+}$ predominates over trivalent $Ce^{3+}$ and wherein said nanoparticles have a diameter of approximately from 3 to 5 nm. The nanoparticles exhibit both superoxide dismutase activity and catalase activity in an environment having a substantially neutral or acidic pH. The nanoparticles may be used to make and may be contained in a medication. The subject nanoparticles are useful in a method of promoting a cytotoxic anti-invasive effect on squamous tumor cells and inhibit tumor invasiveness.

7 Claims, 20 Drawing Sheets

(56) References Cited

U.S. PATENT DOCUMENTS

| | | |
|---|---|---|
| 6,327,074 B1 | 12/2001 | Bass et al. |
| 6,368,577 B1 | 4/2002 | Kropf et al. |
| 6,406,685 B1 | 6/2002 | Philippe |
| 6,468,551 B1 | 10/2002 | Diec |
| 6,497,863 B1 | 12/2002 | Wachter |
| 6,497,875 B1 | 12/2002 | Sorrell et al. |
| 6,501,590 B2 | 12/2002 | Bass et al. |
| 6,592,746 B2 | 7/2003 | Schmid-Schoenbein et al. |
| 6,654,161 B2 | 11/2003 | Bass et al. |
| 6,844,387 B2 | 1/2005 | Bass et al. |
| 6,890,896 B1 | 5/2005 | Shashoua |
| 7,005,504 B2 | 2/2006 | Hsei et al. |
| 7,075,707 B1 | 7/2006 | Rapaport et al. |
| 7,141,227 B2 | 11/2006 | Chan |
| 7,270,813 B2 | 9/2007 | Shimp et al. |
| 7,347,987 B2 | 3/2008 | McGinnis et al. |
| 7,419,516 B1 | 9/2008 | Seal et al. |
| 7,431,758 B2 | 10/2008 | Ota et al. |
| 7,442,686 B2 | 10/2008 | Lasko et al. |
| 7,458,384 B1 | 12/2008 | Seal et al. |
| 7,471,706 B2 | 12/2008 | Bass et al. |
| 7,504,356 B1 | 3/2009 | Self et al. |
| 7,507,480 B2 | 3/2009 | Sugama |
| 7,534,453 B1 | 5/2009 | Rzigalinski et al. |
| 7,563,459 B2 | 7/2009 | Phillips |
| 7,642,250 B2 | 1/2010 | Williams |
| 7,687,505 B2 | 3/2010 | Sugaya |
| 7,725,802 B2 | 5/2010 | Eroz et al. |
| 7,727,559 B2 | 6/2010 | McGinnis et al. |
| 7,772,375 B2 | 8/2010 | Greferath et al. |
| 7,888,119 B2 | 2/2011 | Sugaya et al. |
| 7,899,093 B1 | 3/2011 | Bass et al. |
| 7,906,147 B2 | 3/2011 | Hainfield |
| 7,924,617 B2 | 4/2011 | Yip |
| 7,959,690 B1 | 6/2011 | Seal et al. |
| 7,959,949 B2 | 6/2011 | Seal et al. |
| 8,080,420 B2 | 12/2011 | Sugaya |
| 8,084,096 B1 | 12/2011 | Fei et al. |
| 8,097,270 B2 | 1/2012 | Ketelson et al. |
| 8,153,158 B2 | 4/2012 | Sugaya et al. |
| 8,172,901 B2 | 5/2012 | Altman et al. |
| 8,172,997 B2 | 5/2012 | Seal et al. |
| 2003/0050709 A1 | 3/2003 | Noth et al. |
| 2003/0187077 A1 | 10/2003 | Chane-Ching |
| 2003/0228277 A1 | 12/2003 | Gehlsen |
| 2004/0013658 A1 | 1/2004 | Fulton et al. |
| 2004/0048808 A1 | 3/2004 | Hamdi et al. |
| 2004/0062753 A1 | 4/2004 | Rezania et al. |
| 2005/0036928 A1 | 2/2005 | Katusic et al. |
| 2005/0159820 A1 | 7/2005 | Yoshikawa et al. |
| 2005/0164377 A1 | 7/2005 | Miyabayashi et al. |
| 2005/0171192 A1 | 8/2005 | Gehlsen |
| 2006/0110440 A1 | 5/2006 | Sugaya et al. |
| 2006/0134789 A1 | 6/2006 | Sugaya et al. |
| 2006/0141137 A1 | 6/2006 | Anderson et al. |
| 2006/0246152 A1 | 11/2006 | McGinnis et al. |
| 2006/0280729 A1 | 12/2006 | Mistry |
| 2007/0003621 A1 | 1/2007 | Nangia et al. |
| 2007/0072825 A1 | 3/2007 | Williams |
| 2007/0123996 A1 | 5/2007 | Sugaya et al. |
| 2007/0166311 A1 | 7/2007 | Greferath et al. |
| 2007/0202193 A1 | 8/2007 | McGinnis et al. |
| 2008/0089836 A1 | 4/2008 | Hainfield et al. |
| 2008/0166412 A1 | 7/2008 | Sugaya et al. |
| 2008/0311390 A1 | 12/2008 | Seal et al. |
| 2009/0071848 A1 | 3/2009 | Seal et al. |
| 2009/0087493 A1 | 4/2009 | Dai et al. |
| 2009/0098574 A1 | 4/2009 | Brisson et al. |
| 2009/0127505 A1 | 5/2009 | Seal et al. |
| 2009/0269410 A1 | 10/2009 | McGinnis et al. |
| 2010/0015050 A1 | 1/2010 | Panyam et al. |
| 2010/0098768 A1 | 4/2010 | Andreescu et al. |
| 2010/0151000 A1 | 6/2010 | Thomas et al. |
| 2010/0221344 A1 | 9/2010 | Seal et al. |
| 2010/0247428 A1 | 9/2010 | Kim et al. |
| 2011/0111007 A1 | 5/2011 | McGinnis et al. |
| 2011/0135740 A1 | 6/2011 | Sugaya et al. |
| 2011/0159056 A1 | 6/2011 | Sugaya et al. |
| 2011/0268662 A1 | 11/2011 | Seal et al. |
| 2011/0319259 A1 | 12/2011 | Fei et al. |
| 2012/0070500 A1 | 3/2012 | Cimini et al. |
| 2012/0093931 A9 | 4/2012 | McGinnis et al. |

FOREIGN PATENT DOCUMENTS

| | | |
|---|---|---|
| WO | WO 2006/118954 A2 | 11/2006 |
| WO | WO 2007/002662 A2 | 1/2007 |
| WO | 2008064357 A2 | 5/2008 |
| WO | WO 2008/064357 A2 | 5/2008 |
| WO | WO 2009/132277 A1 | 10/2009 |
| WO | 2009147214 A2 | 12/2009 |

OTHER PUBLICATIONS

JR Griffiths. "Are Cancer Cells Acidic?" British Journal of Cancer, vol. 64, 1991, pp. 425-427.*

O De Wever, P Demetter, M Mareel, M Bracke. "Stromal myofibroblasts are drivers of invasive cancer growth." International Journal of Cancer, vol. 123, 2008, pp. 2229-2238, available Sep. 5, 2008.*

AS Karakoti, NA Monteiro-Riviere, R Aggarwal, JP Davis, RJ Narayan, WT Self, J McGinnis, S Seal. "Nanoceria as Antioxidant: Synthesis and Biomedical Applications." JOM, Mar. 2008, vol. 60(3) pp. 33-37.*

Pubmed Abstract for Karakoti et al. "Nanoceria as Antioxidant: Synthesis and Biomedical Applications." JOM, Mar. 2008, vol. 60(3) pp. 33-37. Pubmed ID: 20617106. http://www.ncbi.nlm.nih.gov/pubmed/20617106 (accessed Dec. 31, 2015). 2 printed pages.*

Dong et al., "Activation of glassy carbon electrodes by dispersed metal oxide particles", J. Electrochem Soc., 1984, pp. 813-819.

Karakoti et al., Direct Synthesis of Nanoceria in Aqueous Polyhydroxyl Solutions, Journal of Physical Chemistry C, vol. 11, 2007, pp. 17232-17240.

Perez et al., Synthesis of Biocompatible Dextran-Coated Nanoceria With pH-Dependent Antioxidant Properties, Small, vol. 4(5), 2008, pp. 552-556.

Karakoti et al., Nanoceria as Antioxidant: Synthesis and Biomedical, JOM (1989) Mar. 1, 2008; 60(3):33037.

Mohammad et al., Antioxidant Properties of Some nanoparticle May Enhance Wound Healing in T2DM Patient, Digest Journal of Nanomaterials and Biostructures vol. 3, No. 4, Dec. 2008, p. 159-162.

Patil et al., Surface-Derivatized Nanoceria With Human Carbonic Anhydrase II Inhibitors and Fluorophores: A Potential Drug Delivery Device, J. Phys. Chem. C. 2007, vol. 111, No. 24, pp. 8437-8442.

Patil et al., Synthesis of Nanocrystalline Ceria Particles for High Temperature oxidation Resistant Coating, Journal of Nanoparticle Research, 2002, vol. 4, pp. 433-438.

Jin et al., Nanoparticle-Medicated Drug Delivery and Gene Therapy, Biotechnol. Prog., 2007, vol. 23, pp. 32-41.

Eck et al, PEGylated Gold Nanoparticles Conjugated to Monoclonal F19 Antibodies as Targeted labeling Agents for Human Pancreatic Carcinoma Tissue, ACS Nano, 2008, vol. 2 (11), pp. 2263-2272.

Nafee et al, Dissertation entitled Cationically-modified nanoparticles for the pulmonary delivery of the telomerase inhibitor 2'-OMethyl RNA for the treatment of lung cancer. Dissertaion zur Erlangung des Grades des Doktors der Naturwissenschaffen der Naturwissenschaftlich-Technischen Fakult't III Chemie, Pharmazie, Bio-und Werkstoffwissenschafen der Universit des Saarlandes, 2008.

Oliver et al., Synthesis of Pegylated Immunonanparticles. Pharmaceutical Research, Aug. 2002, vol. 19, No. 8, pp. 1137-1143.

Otsuka et al., PEGylated nanoparticles for biological and pharmaceutical applications, Advanced Drug Delivery Reviews, 2003, vol. 55, pp. 403-419.

(56) References Cited

OTHER PUBLICATIONS

Qi et al, Redispersible Hybrid Nanopowders: Cerium Oxide Nanoparticle Complexes with Phosphonated-PEG Oligomers, ACS Nano, 2008, vol. 2 (5), pp. 879-888.
Sokolov et al., Real-Time Vital Optical Imaging of Precancer Using Anti-Epidermal Growth Factor Receptor Antibodies Conjugated to Gold Nanoparticles, Cancer Res. , 2003, vol. 63: 1999-2004.
Suh et al., Multifunctional nanosystems at the interface of physical and life sciences, Physicaplus, Apr. 15, 2010, Iss. No. 13.
Suzuki et al., Preparation and Characteristics of Magnetitelabelled Antibody With Use of Poly(ethylene glycol) Derivatives, Biotechnol. Appl. Biochem., 1995, vol. 21, 00 335-345.
Nazem et al., Nanotechnology for Alzheimer's Disease Detection and Treatment, Insciences J. 2011, 1 (4), 169-193.
Pirmohamed et al., Nanoceria exhibit redox state-dependent catalasemimetic activity, Chem. Comm.,2010, 46 pages, 2736-2738, US.
Chen et al., Rare earth nanoparticles prevent retinal degeneratioinal induced by intracellular peroxides, Nature Publishing Group, 2006, pp. 1-9, US.
Tarnuzzer et al., Vacancy Engineered Ceria Nanoatructures for Protection From Radiation-Induced Cellular Damage, nano Lett., vol. 5, No. 12, 205, pp. 2573-2577, US.
Heckert et al., The role of cerium redox state in the SOD mimetic activity of nanoceria, Biomaterials, 29, 2008, pp. 2705-2709, US.
Sokolov, et al. ,"Real-time vital optical imaging of precancer using anti-epidermal growth factor receptor antibodies conjugated to gold nanoparticles." Cancer Res. 2003, vol. 63:1999, 2004.
Niu, J., et al. "Cardiovascular effects of cerium oxide nanoparticles in a transgenic murine model of cardiomyopathy," Cardiovas. Res. Nov. 30, 2006, Nov. 2006, vol. 73, No. 3, pp. 549-559.
Qureshi, M.A., et al. "Increased exhaled nitric oxide following autologous peripheral hemotopietic stem cell transplantation; a potential marker of idopathic pneumonia syndrome," Chest, Jan. 2004, vol. 125, No. 1, pp. 281-287.
Ohgushi, et al., "Stem Cell Technology and Bioceramics: From Cell to Gene Engineering", J. Biomed. Mat. Res. 48: 913-927; 1999.
Dal Maschio, et al., "Influence of Ce3+/Ce 4+ ratio on phase stability and residual stress field in ceria-yttria stabilized zirconia plasma-sprayed coatings", J. Mat. Sci. 27: 5591-5596; 1992.
Ramsfjell, et al., "Distinct Requirements for Optimal Growth and In Vitro Expansion of Human CD341CD382 Bone Marrow Long-Term Culture-Initiating Cells (LTC-IC), Extended LTC-IC, and Murine In Vivo Long-Term Reconstituting Stem Cells", Blood 99: 4093-4102; 1999.
Devasenpathi, et al., "Forming near net shape free-standing components by plasma spraying", Mat. Let. 57: 882-886; 2002.
Imamura, et al. "Drusen, choridal neovascularization and retinal pigment epithelium dysfunction in SOD1-deficient mice: A model of age-related macular degeneration," PNAS, vol. 103, No. 30; 11282-11287 (Jul. 25, 2006).
Hollyfield, et al. "Oxidative damage-induced inflammation initiates age-related macular degeneration," Nature Medicine, vol. 14, pp. 194-198 (2008).
Birch, et al. Age-related macular degeneration: a target for nanotechnology derived medicines. International Journal of Nanomedicine, 2007, 2(1), 65-77.
Maulik, N. Reactive oxygen species drives myocardial angiogenesis? Antioxidants & Redox Signaling, 2006, 8 (11-12) 2161-2168.
Kuchibhatla et al., "Hierarchical assembly of inorganic nanostructure building blocks to octahedral superstructures a true template-free self-assembly", Nanotechnology, 2007, vol. 18, pp. 1-4.
Ohia, et al. "Pharmacological consequences of oxidative stress in ocular tissues," Mutation Research, 2005, 579, 22-36.
Liu, et al. "Subtype lesions of neovascular age-related macular degeneration in Chinese paitents," Braefe's Arch Clin Exp Opthalmol, 2007, 245, 1441-1445.
Silva. "Seeing the benefits of ceria," Nature Nanotechnology, 2006, 1, 92-94.
Hahn, et al. "Maculas affected by Age-Related Macular Degeneration Contain Increased Chelatable Iron in the Retinal Pigment Epithelium and Bruch's Membrane,"Arch. Opthalmol. 2003, 121, 1099-1105.
Haywood, et al. "Inflammation and Angiogenesis in Osteoarthritis," Arthritis & Rheumatism, 2003, 48 (8), 2173-2177.
Chen, et al. Rare Earth Nanoparticles Prevent Retinal Degeneration Induced by Intracellular Peroxides: Nature Nano Technology, 1(2) 142-148 (2006).
Moongkarndi, et al. "Antiproliferation, antioxidation and induction of apoptosis by Garcinia mangostana (mangosteen) on SKBR3 human breast cancer cell line," J. of Ethno-Pharmacology, vol. 90, (2004) pp. 161-166.
Margrain, et al. "Do blue light filters confer protection against age-related macular degeneration?", Progress in Retinal and Eye Research, vol. 23 (2004) pp. 523-531.
Bailey, et al. "Cerium Oxide Nanoparticles Extend Cell Longevity and Act as Free Radical Scavengers," online (retrieved on Apr. 24, 2006) from: http://www.med.miami.edu/mnbws/Rzigalinski11.html.
Tsai, Ming-Shyong. "The Study of the synthesis of nano-grade cerium oxide powder," Materials Letters 58, 2270-2274 (2004).
Rzigalinski, Beverly Ann, et al. "Cerium Oxide nanoparticles increase the lifespan of cultured brain cells and protect against free radical mechanical trauma" FASEB Journal, vol. 17 No. 4-5, Page Abstract No. 377.24 URL, XP008095016 & FASEB Meeting on Experimental Biology: Translating the Genome, San Diego, CA, USA, Apr. 11-15, 2003 ISSN: 0892-6638 *Abstract*.
Cook, et al. "Neuronal Damage induced by polychlorinated biphenyls is partically reversed by cerium oxide nanoparticles" [online] vol. 2003, 2003, XP008095032 Retrieved from the internet: URL http://sfn.scholarone.com/itin2003/main.htm]?new_page_id=126 &abstract_id=14513&p_num=669.13&is_tech=0> [retrieved on Aug. 5, 2008] *abstract*.
Tusnekawa, S., et al. "Lattice relaxation of monosize Ce02-x nanocrystalline particles" Applied Surface Science Elsevier Netherlands, vol. 152, No. 1-2, Nov. 1999, pp. 53-56.
Hooper, Claire, Y., et al. "New treatment in age-related macular degeneration" Clinical & Experimental Opthalmology, Oct. 2003, pp. 376-391.
Qi, et al. "Redispersible Hybrid Nanopowders; Cerium Oxide Nanoparticle complexes with Phosphonated-PEG Oligomers," ACS Nano, 2008, vol. 2(5), pp. 879-888.
Otsuka, et al. "PEGylated nanoparticles for biological and pharmaceutical applications," Advanced Drug Delivery Reviews, 2003, vol. 55, pp. 403-419.
Olivier, et al. "Synthesis of pegylated immunonanoparticles." Pharmaceutical Research, Aug. 2002, vol. 19, No. 8, pp. 1137-1143.
Shui, Y.B., et al. "Morphological observation on cell death an dphagocytosis induced by ultraviolet irradiation in a cultured human lens epithelial cell line," Dec. 2000, vol. 71, pp. 609-618.
Xijuan, et al. "Size-dependent optical properties of nanocrystalline Ce02:Er obtained by combustion synthesis," Sep. 24, 2001, Phys. Chem. Chem Phys., vol. 3, pp. 5266-5269.
Guo, "Green and red upconversion luminescence in Ce02:Er3+ powders produced by 785 nm laser," Jounral of Solid State Chemistry 180, p. 127-131, 2007.
Perez, J. M., et al. "Synthesis of Biocompatible Dextran-Coated Nanoceria with pH-Dependent Antioxidant Properties," Small, vol. 4 No. 5, 2008, pp. 552-556.
Pirmohamed, et al. "Nanoceria exhibit redox state-dependent catalase mimetic activity," Chem. Comm, 2010, 46, pp. 2736-2738.
Nazem, et al. "Nanotechnology for Alzheimer's disease detection and treatment." Insciences J., 2011, vol. 1(4), pp. 169-193.
Karakoti, et al. "Direct Synthesis of Nanoceria in Aqueous Polyhydroxyl Solutions." J. Phys. Chem. C, vol. 111, No. 46, 2007, pp. 17232-17240.
Tarnuzzer, et al. "Vacancy Engineered Ceria Nanostructures for Protection from Radiation-Induced Cellular Damage," Nano Lett, vol. 4, No. 12, pp. 2573-2577.

(56) References Cited

OTHER PUBLICATIONS

Heckert, et al. "The role of cerium redox state in the SOD mimetic activity of nanoceria," Biomaterials, 29, 2008, pp. 2705-2709.

Schubert, et al. "Cerium and yttrium oxide nanoparticles are neuroprotective," Feb. 2006, Biochemical and Biophysical Research Communications, 342, p. 86-91.

Zhang, et al. Cerium oxide nanoparticles: size selective formation and structure analysis, Jan. 2002, Applied Physics Letters, vol. 81, No. 1, p. 127-129.

Patil, et al. "Surface-derived nanoceria with human carbonic anhydrase II inhibitors and flourphores: a potential drug delivery device." J. Phys. Chem. C., 2007, vol. 111, No. 24, pp. 8437-8442.

Patil, et al. "Synthesis of nanocrystalline ceria particles for high temperature oxidation resistant coating," Journal of Nanoparticle Research, 2002, vol. 4: ppl. 433-438.

Jin, et al. "Nanopartical-mediated drug delivery and gene therapy," Biotechnol. Prog, 2007, vol. 23, pp. 32-41.

Eck, et al. "PEGylated gold nanoparticles conjugated to monoclonal F19 antibodies as targeted labeling agents for human pancreatic carcinoma tissue," ACS Nano, 2008, vol. 2(11) pp. 2263-2272.

Nafee. Dissertation entitled "Cationically-modified nanoparticles for the polmonary delivery of the telomerase inhibitor 2'-O-Methyl RNA for the treatment of lung cancer," Dissertation zur Erlangung des Grades des Doktors der, Naturwissenschaftern der Naturwis-senschaftilch-Technischen Fakul't III Chemie, Pharmazie, Bio-und Werstoffwissenschaften der Universit des Saarlandes, 2008.

Suh et al., "Multifunctional nanosystems at the interface of physical and life sciences", Nano Today, 2009, vol. 4, pp. 27-36.

Suzuki et al., "Preparation and characteristics of magnetite labelled antibody with the use of poly(ethylene glycol) derivatives", Biotechnol. Appl. Biochem., 1995, vol. 21, pp. 335-345.

Monte et al., "Inhibition of lymphocyte induced angiogenesis by free radical scavengers", Free Radic Biol Med, 1994, vol. 17, pp. 259-266.

Drisko, J.A. et al., "The use of Antioxidants with First-Line Chemotherapy in Two Cases of Ovarian Cancer", J Am Coll Nut, 2003, vol. 22(2), pp. 118-123.

Korsvik et al., "Superoxide dismutase mimetic properties exhibited by vacancy engineered ceria nanoparticles", Chem. Commun., 2007, pp. 1056-1058.

Yu et al., "Large-scale nonhydrolytic sol-gel synthesis of uniform-sized ceria nanocrystals with spherical, wire, and tadpole shapes", Angew. Chem. Int. Ed., 2005, vol. 44, pp. 7411-7414.

Ahluwalia et al., "Critical role of hypoxia sensor-HIF1 alpha in VEGF gene activation, implication for angiogenesis and tissue injury healing", Current Medicinal Chemistry, 2012, vol. 19, p. 94.

Perez, J.M. et al., "Synthesis of Biocompatible Dextran-Coated Nanoceria with pH-Dependent Antioxidant Properties", 2008, Small, vol. 4, No. 5, pp. 552-556.

Griffiths, J.R., "Are Cancer Cells Acidic?", British Journal of Cancer, 1991, vol. 64, pp. 425-427.

De Wever, O. et al., "Stromal myofibroblasts are drivers of invasive cancer growth", International Journal of Cancer, 2008, vol. 123, pp. 2229-2238.

Lam, M.A., et al., "Nitric Oxide and Nitroxides Can Act as Efficient Scavengers of Protein-Derived Free Radicals", Chem Res. Toxicol, 2008, vol. 21, pp. 2111-2119.

Karakoti, A.S., et al., "Nanoceria as Antioxidant: Synthesis and Biomedical Applications", JOM, 2008, vol. 60(3), pp. 33-37.

Clinicaltrials.gov, "Clinical Trial for the Treatment of Diabetic Foot Ulcers Using a Nitric Oxide Releasing Patch: PATHON", (http://web.archive.org/web/20091130234819/http://clinicaltrials.gov/show/NCT/00428727) published online Nov. 30, 2009.

Deshpande et al., "Size dependency variation in lattice parameter and valency states in nanocrystalline cerium oxides", Appl;ied Physics Letters, 2005, vol. 87, pp. 133113-1-133113-3.

Rasmussen et al., "Penetration of intact skin by quantum dots with diverse physiochemical properties", Toxicological Sciences, 2006, vol. 91, pp. 159-165.

Park et al., "Oxidative stress induced by cerium oxide nanoparticles in cultured BEAS-2B cells", Toxicology, 2008, vol. 245, pp. 90-100.

MSDS from Aldrich for cerium oxide powder bulk product, Feb. 2013, 6 pages.

Kuchibhatla, S. et al., "Hierarchicial assembly of inorganic nanostructure building blocks to octahedral superstructures—atrue template-free self-assembly", Nanotechnology, 2007, vol. 17 pp. 1-4.

Kuchibhatla, S, "Probing and Tuning the Size, Morphology, Chemistry and Structure of Nanoscale Cerium Oxide", Diss. University of Central Florida, 2008, 175 pages.

Giri, S et al., "Nanoceria: A Rare-Earth Nanoparticle as a Novel Anti-Angiogenic Therapeutic Agent in Ovarian Cancer", PLOS ONE, Jan. 2013, vol. 8, Issue 1, e54578.

PCT/US2011/0044329; PCT International Search Report and Written Opinion, Dec. 8, 2011.

De Wever, 0., et al, "Role of tissue stroma in cancer cell invasion." J. Pathol. vol. 200, pp. 429-447 (2003).

Liotta, L. A. , et al, "The microenvironment of the tumour-host interface." Nature vol. 411, pp. 375-379 (2001).

Pupa, S. M. et al. "New insights into the role of extracellular matrix during tumor onset and progression." J. Cell. Physiol. vol. 192, pp. 259-267 (2002).

Cat, B, et al. "Enhancement of tumor invasion depends on transdifferentiation of skin fibroblasts mediated by reactive oxygen species." J. Cell Sci. vol. 119, pp. 2727-2738 (2006).

Kunz-Schughart, et al, "Tumor-associated fibroblasts (part II): functional impact on tumor tissue." Histol. Histopathol. vol. 17, pp. 623-637 (2002).

Desmouliere, A. et al. "The stroma reaction myofibroblast: a key player in the control of tumor cell behavior." Int. J. Dev. Biol. vol. 48: pp. 509-517 (2004).

Cerutti, P. et al. "The role of the cellular antioxidant defense in oxidant carcinogenesis." Environ. Health Perspect. vol. 102, pp. 123-129 (1994).

Freitas, R. A. "What is nanomedicine?" Nanomedicine vol. 1, pp. 2-9 (2005).

Barry, S. E. "Challenges in the development of magnetic particles for therapeutic applications." Int. J. Hyperth. vol. 24, pp. 451-466 (2008).

Corchero, J. L., et al "Biomedical applications of distally controlled magnetic nanoparticles." Trends Biotechnol. vol. 27, pp. 468-476 (2009).

Lin, W. et al. Toxicity of Cerium Oxide Nanoparticles in Human Lung Cancer Cells:, Int. J. of Toxicol., vol. 251 pp. 451-457 (2006).

Ristow, M. "Oxidative metabolism in cancer growth." Curr. Opin. Clin. Nutr. Metab. Care. vol. 9, pp. 339-345 (2006).

Karakoti, A. s. et al. "PEGylated Nanoceria as Radical Scavenger with Tunable Redox Chemistry." J. Am. Chern. Soc. vol. 131, pp. 14144-14145 (2009).

Thannickal, V. J., et al. "Reactive oxygen species in cell signaling." Am. J. Physiol. Lung Cell Mol. Physiol. vol. 279, pp. L1005-L1028 (2000).

Bayreuther K. et al. "Terminal differentiation, aging, apoptosis, and spontaneous transformation in fibroblast stem cell systems in vivo and in vitro." Ann. N. Y. Acad. Sci. vol. 663 1 pp. 167-179 (1992).

Boukamp, P. et al. "Phenotypic and genotypic characteristics of a cell line from a squamous cell carcinoma of human skin." J. Natl. Cancer Inst. vol. 68, pp. 415-427 (1982).

Stuhlmann, D. et al. "Modulation of homologous gap junctional intercellular communication of human dermal fibroblasts via a paracrine factors generated by squamous tumor cells." Carcinogenesis vol. 24, pp. 1737-1748 (2003).

Reynolds, E. S. "The use of lead citrate citrate at high pH as electron opaque stain in electron microscopy." J. Cell Biol. vol. 17, pp. 208-212 (1963).

MocxSMAnn, T. "Rapid colorimetric growth and survival: application to assay for cellular proliferation and cytotoxicity assays. (1983)." J. Immunol. Methods vol. 65, pp. 55-63.

(56) References Cited

OTHER PUBLICATIONS

Speckmann, B. et al. "Selenoprotein P expression is controlled through interaction of the coactivator PGC-1alpha with Fox01a and hepatocyte nuclear factor 4alpha transcription factors." Hepatology vol. 48, pp. 1998-2006 (2008).

Nishimura, M. et al. "Effects of prototypical drug• metabolizing enzyme inducers on mRNA expression of housekeeping genes in primary cultures of human and rat hepatocytes." Biochem. Biophys. Res. Commun. vol. pp. 346, 1033-1039 (2006).

Laemmli, "U K. Cleavage of structural proteins during the assembly of the head of bacteriophage T4." Nature vol. 227, pp. 680-685 (1970).

Mauch, C. et al. "Regulation of collagen synthesis in fibroblasts within a three-dimensional collagen gel." Exp. Cell Res. vol. 178, pp. 493-503 (1988).

Damour, 0. et al. "A dermal substrate made of collagen-GAG-chitosan for deep burn coverage: first clinical uses." Clin. Mater. vol. 15, pp. 273-276 (1994).

Schlotmann, K. et al. "Cosmetic efficacy claims in vitro using a three-dimensional human skin model." Int. J. Cosmet. Sci. vol. 23, pp. 309-318 (2001).

Stuhlmann, D. et al. "Paracrine effect of TGF-beta1 on downregulation of gap junctional intercellular communication between human dermal fibroblasts." Biochem. Biophys. Res. Commun. vol. 319, pp. 321-326 (2004).

Heckert, E. G. et al. "Fenton-like reaction catalyzed by rare earth inner transition metal cerium." Environ. Sci. Technol. vol. 42, pp. 5014-5019 (2008).

Rzigalinski, B. A., et al. "Radical nanomedicine." Nanomedicine vol. 1, pp. 399-412 (2006).

Korsvik, C. et al. "Superoxide dismutase mimetic properties exhibited by vacancy engineered ceria nanoparticles." Chern. Commun. vol. 14, pp. 1056-1058 (2007).

Perez, J. M. et al. "Synthesis of biocompatible dextran-coated nanoceria with pH-dependent antioxidant properties." ASMAII vol. 4, pp. 552-556 (2008).

Auffan, M. et al. "Ce02 nanoparticles induce DNA damage towards human dermal fibroblasts in vi t:ro." Nanotoxicol. vol. 3, pp. 161-171 (2009).

Treiber, N. et al. "Overexpression of manganese superoxide dismutase in human dermal fibroblasts enhances the contraction of free floating collagen lattice: implications for ageing and hyperplastic scar formation." Arch. Dermatol. Res. vol. 301, pp. 273-287 (2009).

Kessler, D. et al. "Fibroblasts in mechanically stressed collagen lattices assume a "synthetic" phenotype." J. Biol. Chern. vol. 276, pp. 36575-36585 (2001).

Arora, P.D., et al. "Dependence of collagen remodelling on alpha-smooth muscle actin expression by fibroblasts." J. Cell. Physiol. vol. 159, pp. 161-175 (1994).

Ljinen, P. et al. "Transforming growth factor-beta 1 promotes contraction of collagen gel by cardiac fibroblasts through their differentiation into myofibroblats." Methods Find. Exp. Clin. Pharmacal. vol. 25, pp. 79-86 (2003).

Levine, R. L., et al. "Carbonyl assays for determination of oxidatively modified proteins." Methods Enzymol. vol. 233, pp. 346-357 (1994).

de Wever, et al, "Role of myofibroblasts at the invasion front." Biol. Chern. vol. 383, pp. 55-67 (2002).

Nadege, D. et al. "Mitochondria: from bioenergetics to the metabolic regulation of carcinogenesis." Front. Biosci. vol. 14, pp. 4015-4034 (2009).

Moller, P. et al. "Role of oxidative damage in toxicity of particulates." Free Radic. Res. vol. 44, pp. 1-46 (2010).

Oberdorster, G. et al. "Nanotoxicology: an emerging discipline evolving from studies of ultrafine particles." Environ. Health Perspect. vol. 113, pp. 823-829 (2005).

Shvedova, A. A. et al. "Exposure to carbon nanotube material: assessment of nanotube cytotoxicity using human keratinocyte cells." J. Toxicol. Environ. Health A vol. 66, pp. 1909-1926 (2003).

Warheit, D. B. "Nanoparticles: Health impacts ? Mater." Today vol. 7, pp. 32-35 (2004).

Heckert, E. et al. "The role of cerium state in the SOD mimetic activity redox of nanoceria." Biomaterials vol. 29, pp. 2705-2709 (2008).

Seo YH, et al, "Profiling protein thiol oxidation in tumor cells using sulfenic acid-specific antibodies." Proceedings of the National Academy of Sciences of the United States of America vol. 106: pp. 16163-16168, 2009.

Sies H. "Strategies of Antioxidant Defense." European Journal of Biochemistry vol. 215: pp. 213-219, 1993.

Sies H, et al, Oxidative Stress—Damage to Intact-Cells and Organs, Philosophical Transactions of the Royal Society of London Series B—Biological Sciences vol. 311: pp. 617-631, 1985.

Stolk J, et al, "Characteristics of the inhibition of NADPH oxidase activation in neutrophils by apocynin, a methoxysubstituted catechol." Am J Respir Cell Mol Biol vol. 11: pp. 95-102, 1994.

Storz P. "Reactive oxygen species in tumor progression." Front Biosci vol. 10: pp. 1881-1896, 2005.

Stuhlmann D, et al, "Modulation of homologous gap junctional intercellular communication of human dermal fibroblasts via a paracrine factor(s) generated by squamous tumor cells." Carcinogenesis vol. 24: pp. 1737-1748, 2003.

Swietach P, et al, "Regulation of tumor pH and the role of carbonic anhydrase 9." Cancer Metastasis Rev vol. 26: pp. 299-310, 2007.

Tang Y, et al, "Caveolin-1 is related to invasion, survival, and poor prognosis in hepatocellular cancer." Med Oncol, vol. 29: pp. 977-984, 2012.

Thannickal VJ, et al, "Tyrosine phosphorylation regulates H2O2 production in lung fibroblasts stimulated by transforming growth factor beta 1." Journal of Biological Chemistry vol. 273: pp. 23611-23615, 1998.

Thannickal VJ, et al, "Reactive oxygen species in cell signaling." American Journal of Physiology-Lung Cellular and Molecular Physiology vol. 279: pp. L1005-L1028, 2000.

Thompson TC, et al, "The role of caveolin-1 in prostate cancer: clinical implications." Prostate Cancer Prostatic Dis vol. 13: pp. 6-11, 2010.

Tomayko MM, et al, "Determination of Subcutaneous Tumor Size in Athymic (Nude) Mice." Cancer Chemotherapy and Pharmacology vol. 24: pp. 148-154, 1989.

Valko M, et al, "Free radicals and antioxidants in normal physiological functions and human disease." Int J Biochem Cell Biol vol. 39: pp. 44-84, 2007.

Wittgen HG, et al. "Reactive oxygen species in melanoma and its therapeutic implications." Melanoma Res vol. 17: pp. 400-409, 2007.

Woiniak A, et al, "The effect of antitumor drugs on oxidative stress in B16 and S91 melanoma cells in vitro." Med Sci Monit vol. 11: pp. BR22-9, 2005.

Zhou M, et al, "A stable nonfluorescent derivative of resorufin for the fluorometric determination of trace hydrogen peroxide: applications in detecting the activity of phagocyte NADPH oxidase and other oxidases." Anal Biochem vol. 253: pp. 162-168, 1997.

Zhou, X.D. et al., "Processing of Nanometer-Scale CeO2 Particles", Chem. Mater., 2003, vol. 15, pp. 378-382.

Ades EW, et al, HMEC-1: "establishment of an immortalized human microvascular endothelial cell line." J Invest Dermatol vol. 99: pp. 683-690, 1992.

Alili L, et al, "Suppression of tumor invasion by inorganic nanoparticles." Cancer Research vol. 69 pp. (23 Suppl.): Boston, C42, 2009.

Alili L, et al, "Combined cytotoxic and anti-invasive properties of redox-active nanoparticles in tumor-stroma interactions." Biomaterials vol. 32: pp. 2918-2929, 2011.

Altekruse SF, et al, "SEER Cancer Statistics Review", 1975-2007. National Cancer Institute. Bethesda, MD, 2010.

Bardos Ji, et al, "Negative and positive regulation of HIF-1: a complex network." Biochim Biophys Acta vol. 1755: pp. 107-120, 2005.

Bayreuther K, et al "Terminal differentiation, aging, apoptosis, and spontaneous transformation in fibroblast stem cell systems in vivo and in vitro." Ann N Y Acad Sci vol. 663: pp. 167-179, 1992.

(56) References Cited

OTHER PUBLICATIONS

Bhatia S, et al, "Treatment of metastatic melanoma: an overview." Oncology (Williston Park) vol. 23: pp. 488-496, 2009.

Boulares AH, et al, "Role of poly(ADP-ribose) polymerase (PARP) cleavage in apoptosis. Caspase 3-resistant PARP mutant increases rates of apoptosis in transfected cells." J Biol Chem vol. 274: pp. 22932-22940, 1999.

Brenneisen P, et al, "Central role of Ferrous/Ferric iron in the ultraviolet B irradiation-mediated signaling pathway leading to increased interstitial collagenase (matrix-degrading metalloprotease (MMP)-1) and stromelysin-1 (MMP-3) mRNA levels in cultured human dermal fibroblasts." J Biol Chem vol. 273: pp. 5279-5287, 1998.

Celardo I, et al, "Cerium oxide nanoparticles: a promise for applications in therapy." J Exp Thor Oncol vol. 9: pp. 47-51, 2011.

Deshpande S, et al, "Size dependency variation in lattice parameter and valency states in nanocrystalline cerium oxide." Appl. Phys. Lett. vol. 87, pp. 133113, 2005.

Deshpande S, et al, "Size dependency variation in lattice parameter and valency states in nanocrystalline oxide." Appl. Phys. Lett. 87, pp. 133113, 2005.

De Wever O, et al, "Role of myofibroblasts at the invasion front." Biological Chemistry vol. 383: pp. 55-67, 2002.

Fang J, et al, "Tumor-targeted induction of oxystress for cancer therapy." J Drug Target. vol. 15: pp. 475-486, 2007.

Freitas RA, Jr. "What is nanomedicine?" Nanomedicine vol. 1: pp. 2-9, 2005.

Fruehauf JP, et al, "Reactive oxygen species: an Achilles' heel of melanoma?" Expert Rev Anticancer Ther vol. 8: pp. 1751-1757, 2008.

Gao W, et al, "Effect of gold nanoparticles on glutathione depletion-induced hydrogen peroxide generation and apoptosis in HL7702 cells." Toxicol Lett vol. 205: pp. 86-95, 2011.

Garbe C, et al, "Melanoma epidemiology and trends." Clin Dermatol vol. 27: pp. 3-9, 2009.

Garbe C, et al, "Treatment of melanoma." Dtsch Arztebl Int vol. 105: pp. 845-851, 2008.

Giard DJ, et al, "In vitro cultivation of human tumors: establishment of cell lines derived from a series of solid tumors." J Natl Cancer Inst vol. 51: pp. 1417-1423, 1973.

Heckert EG, et al, "The role of cerium redox state in the SOD mimetic activity of nanoceria." Biomaterials vol. 29: pp. 2705-2709, 2008.

Helmlinger G, et al, "Interstital pH and pO2 gradients in solid tumors in vivo: high-resolution measurements reveal a lack of correlation." Nat Med vol. 3: pp, 177-182, 1997.

Jahroudi N, et al, "The role of endothelial cells in tumor invasion and metastasis." J Neurooncol vol. 23: pp. 99-108, 1995.

Jemal A, at al, "Cancer statistics", 2008. CA Cancer J Clin vol. 58: pp. 71-96, 2008.

Kappus H, et al, "Toxic drug effects associated with oxygen metabolism: redox cycling and lipid peroxidation." Experientia vol. 37: pp. 1233-1241, 1981.

Karakoti AS, et al, "Direct synthesis of nanoceria in aqueous polyhydroxyl solutions." Journal of Physical Chemistry C vol. 111: pp. 17232-17240, 2007.

Karakoti AS, et al, "Nanoceria as Antioxidant: Synthesis and Biomedical Applications." Jom (1989) vol. 60: pp. 33-37, 2008.

Karakoti AS, et al, "Redox-active radical scavenging nanomaterials." Chem Soc Rev. vol. 39: pp. 4422-4432, 2010.

Kawiak A, et al, "Induction of Apoptosis in HL-60 Cells through the ROS-Mediated Mitochondrial Pathway by Ramentaceone from Drosera aliciae." Journal of Natural Products vol. 75: pp. 9-14, 2012.

K. Kawiak et al, "Induction of Apoptosis in HL-60 Cells through the ROS-Mediated Mitochondrial Pathway by Ramentaceone from Drosera aliciae." Journal of Natural Products vol. 75: pp. 9-14, 2012. ietzmann T, et al, "Reactive oxygen species in the control of hypoxia-inducible factor-mediated gene expression." Semin Cell Dev Biol vol. 16: pp. 474-486, 2005.

Korsvik C, et al, "Superoxide dismutase mimetic properties exhibited by vacancy engineered ceria nanoparticles." Chem Commun (Camb): pp. 1056-1058, 2007.

Kuchibhatla S, et al, "One dimensional nanostructured materials." Progress in Materials Science vol. 52: pp. 699-913, 2007.

Laemmli UK. Cleavage of structural proteins during the assembly of the head of bacteriophage T4 Nature vol. 227: pp. 680-685, 1970.

Laurent A, et al, "Controlling tumor growth by modulating endogenous production of reactive oxygen species." Cancer Res vol. 65: pp. 948-956, 2005.

Levi F, et al, "High constant incidence rates of second primary neoplasms." Eur J Cancer Prev vol. 17: pp. 385-388, 2008.

Li P, et al, "Cytochrome c and dATP-dependent formation of Apaf-1/caspase-9 complex initiates an apoptotic protease cascade." Cell vol. 91: pp. 479-489, 1997.

Lin W, et al, "Toxicity of cerium oxide nanoparticles in human lung cancer cells." Int J Toxicol vol. 25: pp. 451-457, 2006.

Luanpitpong S, et al, "Regulation of lung cancer cell migration and invasion by reactive oxygen species and caveolin-1." J Biol Chem vol. 285: pp. 38832-38840, 2010.

Malecki JM, et al, "LY294002 and olomoucine synergize in promoting death of melanoma cells through activation of caspase-3 and apoptosis." Melanoma Res. vol. 20: pp. 52-58, 2010.

Mosmann T. "Rapid colorimetric assay for cellular growth and survival: application to proliferation and cytotoxicity assays." J Immunol Methods vol. 65: pp. 55-63, 1983.

Nagata S. "Apoptosis by death factor." Cell vol. 88: pp. 355-365, 1997.

Nangaku M, et al, "A novel class of prolyl hydroxylase inhibitors induces angiogenesis and exerts organ protection against ischemia." Arterioscler Thromb Vasc Biol vol. 27: pp. 2548-2554, 2007.

Parums DV, et al, "JC70: a new monoclonal antibody that detects vascular endothelium associated antigen on routinely processed tissue sections." J Clin Pathol vol. 43: pp. 752-757, 1990.

Pirmohamed T, et al, "Nanoceria exhibit redox state-dependent catalase mimetic activity." Chem. Commun. vol. 46: pp. 2736-273, 2010.

Quiles JL, et al, "Antioxidant nutrients and adriamycin toxicity." Toxicology vol. 180: pp. 79-95, 2002.

Reynolds ES. "Use of Lead Citrate at High Ph as an Electron-Opaque Stain in Electron Microscopy." Journal of Cell Biology vol. 17: pp. 208, 1963.

Roberts RA, et al, "Toxicological and pathophysiological roles of reactive oxygen and nitrogen species." Toxicology vol. 276: pp. 85-94, 2010.

Ruas JL, et al, "Hypoxia-dependent activation of HIF into a transcriptional regulator." Semin Cell Dev Biol vol. 16: pp. 514-522, 2005.

Sanchez Y, et al, "Regulation of genistein-induced differentiation in human acute myeloid leukaemia cells (HL60, NB4) Protein kinase modulation and reactive oxygen species generation." Biochemical Pharmacology vol. 77: pp. 384-396, 2009.

Saphir A. "Angiogenesis: the unifying concept in cancer?" J Natl Cancer Inst vol. 89: pp. 1658-1659, 1997.

* cited by examiner

REDOX ACTIVE CERIUM OXIDE NANOPARTICLES AND ASSOCIATED METHODS

CROSS-REFERENCE TO RELATED APPLICATION

This application is a continuation of application Ser. No. 12/834,302, filed Jul. 12, 2010, which claims the benefit of Provisional Application No. 61/224,602, filed on Jul. 10, 2009. Each of these applications is hereby incorporated by reference in its entirety.

STATEMENT REGARDING FEDERALLY SPONSORED RESEARCH OR DEVELOPMENT

This invention was made with government support by the National Science Foundation under award #CBET07081712. The government has certain rights in the invention.

SEQUENCE LISTING

This application contains a Sequence Listing electronically submitted via EFS-web to the United States Patent and Trademark Office as a text file named "Sequence_Listing.txt." The electronically filed Sequence Listing serves as both the paper copy required by 37 C.F.R. §1.821(c) and the computer readable file required by 37 C.F.R. §1.821(c). The information contained in the Sequence Listing is incorporated herein by reference in its entirety.

FIELD OF THE INVENTION

The invention relates to the field of nanomedicine and, more particularly, to cerium oxide nanoparticles displaying redox functionality and useful for inhibiting tumor cells while not affecting normal cells, and associated methods.

BACKGROUND

Many studies on neoplastic transformation and tumor progression focused and still focus on tumor cells. However, one important aspect in tumor progression is the interaction between cancer cells and the stromal microenvironment [1]. The stroma was initially thought to have only supportive function in tumor development, but there is increasing evidence that stromal components actively take part in tumor progression and, therefore, are major players in tumor invasion [2-4]. Beside inflammatory and endothelial cells another crucial cellular component of the stroma is the myofibroblast (MF), a modulated fibroblast which has acquired the capacity to express the biomarker alpha-smooth muscle actin (αSMA) [5]. Myofibroblasts remodel the connective tissue during wound healing, but also interact with cancer cells at all stages of tumor progression and may thus control such phenomena as tumor invasion and angiogenesis [6].

Although it is known that reactive oxygen species (ROS) can be key regulators at all stages of cancer development [7], the molecular mechanisms underlying the ROS-dependent tumor-stroma interaction in tumor progression and its potential therapeutic modulation to prevent tumor invasion have not been fully elucidated until recently. A better understanding of the ROS initiated molecular mechanisms mediating interaction between the tumor and the tumor microenvironment would be helpful for the development of novel therapeutic strategies, as invasion and metastases are the most common problems in cancer therapy.

Nanomedicine, the medical application of nanotechnology, deals with the application of structures of the size 100 nanometers or smaller in at least one dimension and seeks to deliver a valuable set of research tools and clinically helpful devices in the near future [8]. The small size of nanoparticles endows them with properties that can be very useful in carcinogenesis, particularly in imaging and anti-cancer therapy. A nanoparticle-based therapeutic approach may have the potential as supplementation therapy supporting the classical anticancer strategies such as radiation or the use of anticancer drugs. If future studies show that a nanoparticle-based anticancer therapy has less harmful effects, it is aimed for the application of nanoparticles as major anticancer approach. In both cases, the treatment with nanoparticles should result in killing tumor cells or in prevention of tumor invasion while leaving normal healthy cells intact.

In that context, nano-sized magnetic iron particles are increasingly being used in cancer therapy. Once uptaken by tumor cells, such particles can be magnetically heated leading to localized cell death while healthy cells remain alive [9,10]. Free oxygen radicals generated by exposure to cerium oxide nanoparticles (CNP) produced significant oxidative stress, which killed lung carcinoma cells [11]. However, the toxicity of CNP is still controversial as an antioxidant function of CNP is described as well. Vacancy engineered CNP exhibited superoxide dismutase mimetic activity in human epidermal keratinocytes [12] and in a cell-free test tube system [13].

SUMMARY

With the foregoing in mind, the present invention advantageously provides cerium oxide nanoparticles which are capable of inhibiting tumor cancer cells while being inoffensive to normal cells. As it was described earlier that TGFβ1 increased the intracellular superoxide ($O_2^-$) concentration via activation of NAD(P)H oxidase in human lung [14], and skin fibroblasts [4], the effect of CNP in context of prevention of myofibroblast formation and tumor invasion in tumor-stroma interaction was evaluated for skin-derived tumor cells. In an in-vitro cell culture model and dermis equivalent, nanoparticles of cerium oxide exhibit an inhibitory effect on the formation of myofibroblasts. Furthermore, concentrations of cerium oxide being non-toxic on normal cells showed an inhibitory, even cytotoxic and anti-invasive effect on squamous tumor cells. To our knowledge, this is the first report indicating a dual functionality of cerium oxide nanoparticles in tumor-stroma interaction.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

Figure 1:
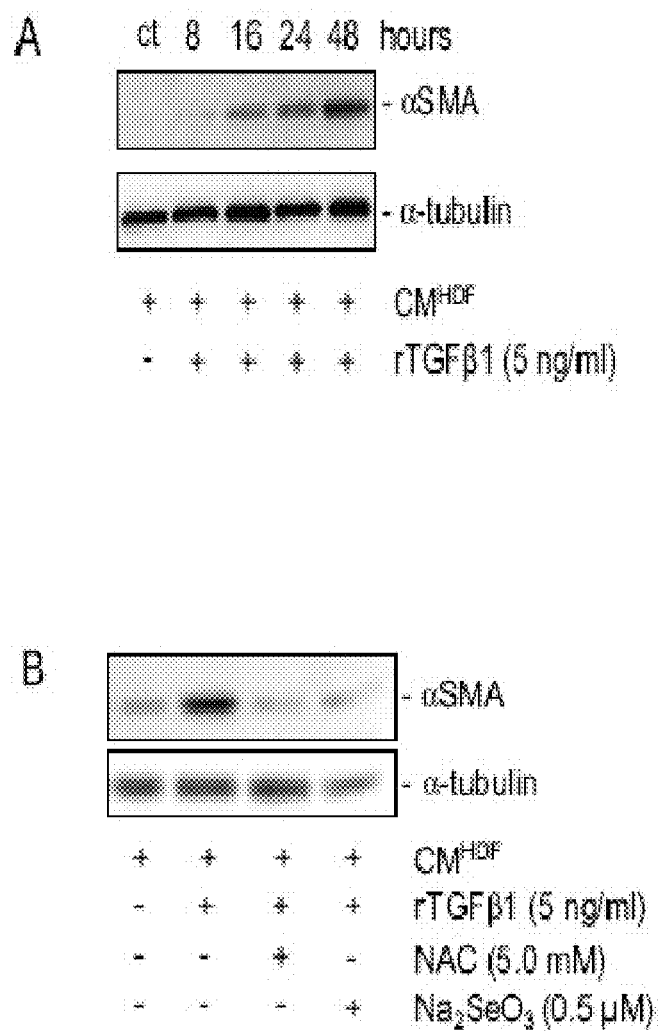
FIG. 1A shows the TGFβ1-mediated transition of fibroblasts to myofibroblasts; subconfluent human dermal fibroblasts (HDF) were cultured in control conditioned medium (CMHDF) and treated with rTGFβ1 (5 ng/ml) CMHDF for various periods of time; the amount of αSMA protein was determined by western blot analysis; experiments were performed in triplicate; the abbreviation CM stands for conditioned medium.
FIG. 1B depicts that antioxidants downregulate the TGFβ1-mediated expression of αSMA; subconfluent HDF were cultured in $CM^{HDF}$ and either untreated or pretreated for 4 h with NAC (5.0 mM) or for 24 h with $Na_2SeO_3$ (0.5 µM) before addition of rTGFβ1 (5 ng/ml); TGFβ1 and the antioxidants were present for an additional 48 h; the amount of SMA protein was detected by western blotting; three independent experiments were performed.
FIG. 1C illustrates that antioxidants increase invasion of tumor cells; subconfluent SCL-1 tumor cells were cultured in $CM^{HDF}$ and either untreated or pretreated for 4 h with NAC (5.0 mM) or for 24 h with $Na_2SeO_3$ (0.5 µM); the invasive capacity of these cells was tested with conditioned media of HDF ($CM^{HDF}$) and myofibroblasts ($CM^{MF}$) as described in Materials and Methods.
Figure 1:
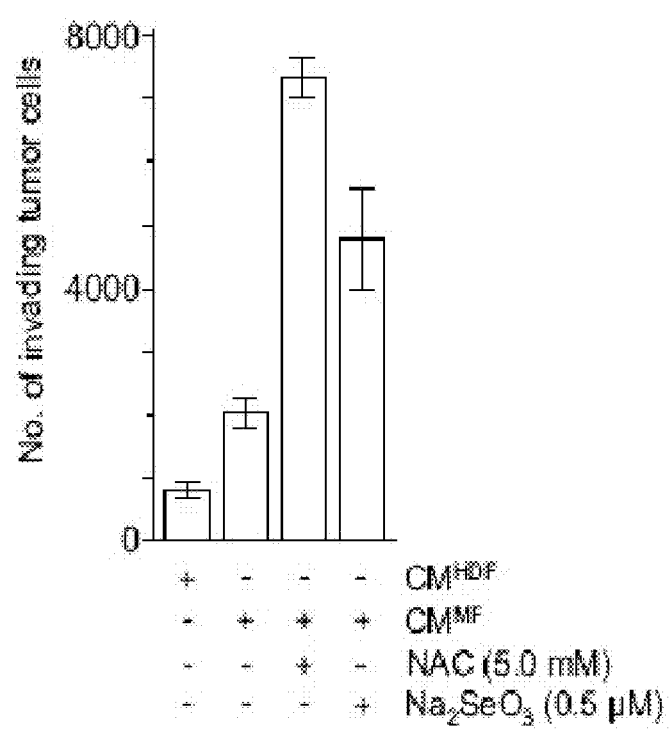

The present invention will now be described more fully hereinafter with reference to the accompanying drawings, in which preferred embodiments of the invention are shown.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not the only ones suitable for use in the invention.

Moreover, it should also be understood that any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Further, any publications, patent applications, patents, and other references mentioned herein are incorporated by reference in their entirety as if they were part of this specification. However, in case of conflict, the present specification, including any definitions, will control. In addition, the materials, methods and examples given are illustrative in nature only and not intended to be limiting.

Accordingly, this invention may be embodied in many different forms and should not be construed as limited to the illustrated embodiments set forth herein. Rather, these illustrated embodiments are provided so that this disclosure will be thorough, complete, and will fully convey the scope of the invention to those skilled in the art. Other features and advantages of the invention will be apparent from the following detailed description, and from the claims.

Materials and Methods

Cell culture media (Dulbecco's modified Eagle's medium (DMEM) was purchased from Invitrogen (Karlsruhe, Germany) and the defined fetal calf serum (FCS gold) was from PAA Laboratories (Linz, Austria). All chemicals including protease as well as phosphatase inhibitor cocktails 1 and 2 were obtained from Sigma (Taufkirchen, Germany) or Merck Biosciences (Bad Soden, Germany) unless otherwise stated. The protein assay kit (Bio-Rad DC, detergent compatible) was from BioRad Laboratories (München, Germany), N-acetyl-L-cysteine (NAC) and sodium selenite were from Merck Biosciences. Matrigel and polycarbonate cell culture inserts (6.5 mm diameter, 8 μm pore size) were delivered from BD Biosciences (Heidelberg, Germany). The Oxyblot Protein Oxidation Detection kit was from Millipore (Schwalbach, Germany). The enhanced chemiluminescence system (SuperSignal West Pico/Femto Maximum Sensitivity Substrate) was supplied by Pierce (Bonn, Germany). Monoclonal mouse antibody raised against human-αSMA and α-tubulin were supplied by Sigma. Polyclonal rabbit antibody raised against human HIF-1 was supplied by New England Biolabs (Frankfurt a.M., Germany). The following secondary antibodies were used: polyclonal horseradish peroxidase (HRP)-conjugated goat anti-mouse IgG antibody (DAKO, Glostrup, Denmark) and anti-rabbit immunoglobulin G antibodies were from Dianova (Hamburg, Germany). Recombinant human TGFβ1 (rTGFβ1) was from R&D Systems (Wiesbaden, Germany).

Cell Culture

Human dermal fibroblasts (HDF) were established by outgrowth from foreskin biopsies of healthy human donors with an age of 3-6 years. Cells were used in passages 2-12, corresponding to cumulative population doubling levels of 3-27 [15]. Dermal fibroblasts and the squamous carcinoma cell line SCL-1, originally derived from the face of a 74-year-old woman [16] (generously provided by Prof. Dr Norbert Fusenig, DKFZ Heidelberg, Germany), were cultured as described [17]. Myofibroblasts (MF) were generated by treatment of HDFs with different concentrations of recombinant TGFβ1 (5 ng/ml) for 48 h in HDF conditioned medium (CMHDF) [4].

Preparation of Conditioned Medium

Conditioned medium was obtained from human dermal fibroblasts ($CM^{HDF}$) and myofibroblasts ($CM^{MF}$). For this, seeded 1.5×10$^6$ HDF cells were grown to subconfluence (~70% confluence) in 175-cm$^2$ culture flasks. The serum-containing medium was removed, and after washing in phosphate-buffered saline (PBS) the cells were incubated in serum-free DMEM or treated with rTGFβ1 (5 ng/ml) in serum-free DMEM for 48 hours. This medium was removed, and after washing in PBS all cells were incubated in 15 ml serum-free DMEM for a further 48 hours before collection of the conditioned medium of HDF ($CM^{HDF}$) and myofibroblasts ($CM^{MF}$).

To prevent myofibroblast formation, HDF were treated with rTGFβ1 (5 ng/ml) in $CM^{HDF}$ in combination with CNP for 48 h. The conditioned medium ($CM^{HDF,TGF,CNP}$) was collected as described above. Conditioned media were used fresh or stored at −20° C. for at the most 2 weeks before use.

Synthesis of Cerium Oxide Nanoparticles

Cerium oxide nanoparticles were synthesized in water and in dextran (molecular weight: 1000 Da) using previously described methods. Briefly, cerium nitrate hexahydrate was dissolved in deionized water and the pH of the solution was maintained between 3.5 to 4.0 for water based nanoparticles. Stoichiometric amounts of hydrogen peroxide and ammonium hydroxide were added to oxidize the dissolved cerium ions as cerium oxide nanoparticles (CNPs). The pH of the solution needs to be maintained below 4.0 to avoid precipitation of CNPs. For synthesis of dextran coated nanoparticles stoichiometric amounts of dextran was first dissolved in deionized water followed by cerium nitrate hexahydrate. The solution was stirred for 2 h followed by addition of ammonium hydroxide (30% w/w). The pH of the solution was kept below 9.5 to avoid precipitation of cerium hydroxide. The resulting cerium oxide nanoparticles were analyzed using UV-visible spectroscopy for determining the oxidation state of nanoparticles and transmission electron microscopy for particle size.

UV-Visible Spectrophotometry

The UV-visible spectral data were obtained using Varian Lambda 750 UV-VIS NIR instrument with a diffuse reflectance detector. The spectra were recorded immediately after the synthesis and after the complete aging treatment of nanoparticles. Deionized water and dextran solution was used as the control for water based CNPs and dextran-stabilized CNPs respectively. The reversal of oxidation state of nanoparticles confirms the presence of higher concentration of CNPs with trivalent oxidation states in water-synthesized nanoparticles.

High Resolution Transmission Electron Microscopy (HR-TEM)

High resolution transmission electron micrographs were obtained using FEI Tecnai F 30 microscope operated at 300 kV with a point-to-point resolution of 0.2 nm. The samples were prepared by depositing a drop of CNP in water and dextran on a carbon coated copper grid. The grids were dried overnight in vacuum before imaging.

Cellular Uptake of Nanoparticles

Serum-starved human dermal fibroblasts in Dulbecco's Modified Eagle Medium (DMEM) were treated with 150 µM $CeO_2$/dextran for 48 h. Thereafter, cells were harvested and washed with phosphate-buffered saline (PBS) to remove excess media. As $CeO_2$/dextran is not detectable by phase contrast microscopy, transmission electron microscopy was used to determine the cellular uptake of nanoceria. For electronmicroscopy, pelleted samples of cerium oxide-treated cells were fixed for 2 h in 4% paraformaldehyde and 2.5% glutaraldehyde (Serva, Heidelberg, Germany) in 0.1 M phosphate buffer at pH 7.4 at room temperature. Next, the pellets were thoroughly washed with four changes of PBS, followed by a postfixation for 60 min in 1% osmium tetroxide (Serva) in the same buffer. The specimens were dehydrated in a graded series of acetone, and embedded in Spurr's medium (Serva) at 70° C. for 24 h.

Ultrathin sections were cut from the embedded tissue with a Reichert Ultracut (Vienna, Austria) using a diamond knife. The sections were collected on coated copper grids, and subsequently stained with uranyl acetate and lead citrate according to earlier published data [18]. The grids were analyzed using a Hitachi H 600 electron microscope. Documentation was carried out by using an optical system and the Digital Micrograph software (Gatan, Munich, Germany). For light microscopical controls semithin section were cut and stained with 1% Toluidine blue and 1% Borax.

Injection and Determining Cerium Oxide Nanoparticles in Skin

Eight-week-old, CD-1 mice were divided into two groups. Controls were given weekly doses of 100 µl sterile PBS only by intravenous (IV) administration. The nanoceria group received five doses (one dose a week) of 0.5 mg/kg of nanoceria suspended in 100 µl of sterile saline (IV). Both groups were sacrificed on the sixth week. Skin tissue from the back of each animal was excised and hair removed. The tissue was patted dry, weighed and placed in 70% nitric acid overnight to start the digestion process. Samples were then microwave digested. The temperature was ramped to 200° C. over 20 min and held there for another 20 min. Samples were then boiled down to less than 1 ml each and reconstituted in water to an exact volume of 10 ml. Cerium levels were assessed using inductively coupled plasma mass spectroscopy (ICP-MS).

Cell Viability

The cytotoxic effect of cerium oxide nanoparticles (CNP) was measured by the MTT (3-(4,5-Dimethylthiazol-2-yl)-2, 5-diphenyltetrazolium bromide) assay [19]. The activity of mitochondrial dehydrogenases, as indicator of cellular viability, results in formation of a purple formazan dye. Briefly, MTT solution (0.5 mg/ml) was added to the cell cultures treated for various times with the nanoparticles. The cells were incubated for an additional 1 hour. The medium was removed and the cells were lysed in dimethyl sulfoxide. Formazan formation was measured at 570 nm. The results were shown as a percentage of mock-treated control which was set at 100%.

RNA Isolation and Quantitative Real-Time RT-PCR

Total RNA was isolated and transcribed into cDNA as described [20]. Expression of mRNA was analyzed by real-time RT-PCR using a LightCycler system (Roche; Mannheim, Germany) as described [20]. Real-time RT-PCR was performed with 40 ng cDNA in glass capillaries containing LightCycler FastStart DNA Master SYBR Green I Reaction Mix (Roche), 2 mM $MgCl2$ and 1 µM of primers. Quantitation of the PCR amplicons was performed using the LightCycler Software. Hypoxanthine phosphoribosyltransferase (HPRT1) was used as internal normalization control [21]. Sequences of primer pairs are given in Table 1.

SDS-PAGE and Western Blotting

SDS-PAGE was performed according to the standard protocols published elsewhere [22] with minor modifications. Briefly, cells were lysed after incubation with rTGFβ1 in 1% SDS with 1:1000 protease inhibitor cocktail (Sigma; Taufkirchen, Germany). After sonication, the protein concentration was determined by using a modified Lowry method (Bio-Rad DC). 2×SDS-PAGE sample buffer (1.5 M Tris-HCl pH 6.8, 6 ml 20% SDS, 30 ml glycerol, 15 ml β-mercaptoethanol and 1.8 mg bromophenol blue was added, and after heating, the samples (10 µg total protein/lane) were applied to 10% (w/v) SDS-polyacrylamide gels. After electroblotting, immunodetection was carried out (1:1000 dilution of primary antibodies (mouse monoclonal anti-SMA and tubulin), 1:20000 dilution of anti-mouse antibody conjugated to HRP). Antigen-antibody complexes were visualized by an enhanced chemiluminescence system. Alpha-tubulin was used as internal control for equal loading.

Preparation of Collagen Lattices and Dermal Equivalents

Three-dimensional collagen lattices were prepared as described [23] with minor modifications. Briefly, type I collagen from rat tail tendon was redissolved at 3.2 mg/ml in sterile 0.2% acetic acid. Human dermal fibroblasts were seeded at $1.25 \times 10^5$ cells/ml into a NaOH-neutralized solution containing 0.8 mg collagen/ml 1×DMEM with 5% FCS and grown for 24 h at 37° C. in 3.5-cm-diameter uncoated bacterial culture dishes. Cells in that mechanically relaxed lattices were allowed to contract the gel matrix. The medium was replaced by serum-free medium or serum-free medium containing non-toxic concentrations of CNP, and the collagen lattices incubated for a further 24 h before addition of recombinant TGFβ1. After 48 h each collagen lattice was photographed and the diameter (in cm) used as a measure of the contractile force of the (myo)fibroblasts.

The dermal equivalents (DE) were prepared as previously described [24, 25]. Briefly, a suspension of 2×105 dermal fibroblasts/cm$^2$ was added in each well of a 24-well plate on top of a collagen-chitosan-glycosaminoglycan (cc-GAG) biopolymer and the DE was cultured for 14 d in DMEM plus 10% FCS containing 50 µg/ml ascorbic acid under submerged conditions in a humidified atmosphere. The medium was changed every 2 d. DE were fixed in 4% paraformaldehyde and embedded in paraffin. Sections of 6 µm thickness were stained using hematoxylin-eosin (HE). In addition, DE were incubated for 2 d with recombinant TGFβ1 or in combination with 150 µM CNP. Thereafter, the DE were washed in PBS and digested with 3 mg *Clostridium histolyticum* collagenase/ml PBS for 30-45 min at 37° C. After centrifugation, the cells were lysed with 1:1000 diluted protease and phosphatase inhibitors and subjected to western blot analysis.

Invasion Assay

Cell culture inserts (transwells) were overlaid with 125 µg/ml growth factor reduced Matrigel and placed in a 24-well plate. SCL-1 tumor cells ($5 \times 10^4$ cells/insert) either mock-treated or pretreated with antioxidants (NAC, selenite) or CNP were seeded on top of the matrigel in serum-free DMEM. $CM^{HDF}$, $CM^{MF}$, or $CM^{HDF,TGF,CNP}$ (see above) were used as chemoattractant in the lower chamber. After 72 h at 37° C., the tumor cells were rubbed off the upper side of the filter using cotton swabs, and the SCL-1 cells, which invaded to the lower side of the insert, were stained with Coomassie Blue solution (0.05% Coomassie Blue, 20% MeOH, 7.5% acetic acid). The number of invaded cells was estimated by counting 25 random microscopic fields/insert.

Determination of Oxidized (Carbonylated) Proteins Oxyblot Analysis

Dermal fibroblasts or tumor cells were grown to subconfluence on tissue culture dishes. After removal of serum-containing medium, HDF were cultured in $CM^{HDF}$ and either mock-treated or pretreated for 40 h with 150 µM $CeO_2$ nanoparticles prior to addition of 10 ng rTGFβ1/ml for additional 8 h. Tumor cells were mock-treated or treated with 150 µM CNP for 16 h. As positive control, the cells were treated with 250 µM $H_2O_2$ for 1 h. Thereafter, cells were lysed and carbonyl groups of oxidized proteins were detected with the OxyBlot™ Protein Oxidation Detection Kit, following the manufacturer's protocol. Briefly, the protein concentration was determined by using a modified Lowry method (Bio-Rad DC). The protein amounts of the samples were aligned. 5 µg of this cell lysate was incubated with 2,4-dinitrophenyl (DNP) hydrazine to form the DNP hydrazone derivatives. Labeled proteins were separated by SDS-PAGE and immunostained using rabbit anti-DNP antiserum (1:500) and goat anti-rabbit IgG conjugated to horseradish peroxidase (1:2000). Blots were developed by enhanced chemiluminescence.

Measurement of Intracellular ROS

Generation of ROS was determined using 2',7'-Dichlorodihydrofluorescein diacetate ($H_2DCF$-DA), a dye that diffuses across the lipid membranes into cells and is subsequently oxidized by intracellular ROS forming the highly fluorescent DCF. Subconfluent HDF and SCL-1 tumor cells were exposed to 50 µM or 150 µM CNP in serum-free DMEM in 24-well plates. Untreated subconfluent SCL-1 cells were used as negative controls. Medium was substituted after 24 h by 100 µM H2DCF-DA containing Hanks Balanced Salt Solution (HESS). DCF fluorescence was detected at an excitation wavelength of 485 nm and emission wavelength of 520 nm in 15 minutes intervals in a FLUOstar OPTIMA plate reader (BMG Labtech, Offenburg, Germany). Mean fluorescence intensities and standard error of mean were determined for each reading point by using the statistical software Prism 3.0 (GraphPad, San Diego, Calif., USA).

Statistical Analysis

Means were calculated from at least three independent experiments, and error bars represent standard error of the mean (s.e.m.). Analysis of statistical significance was done by Student t test or ANOVA with $*P<0.05$, $P<0.01$, and $*P<0.001$ as levels of significance.

Table 1 Sequences of Primers for real-time RT-PCR
Genes Primer (5'-3')
αSMA Forward: CTGTTCCAGCCATCCTTCAT (SEQ ID NO: 1)
Reverse: TCATGATGCTGCTGTTGTAGGTGGT (SEQ ID NO: 2)
HPRT1 Forward: ATTCTTTGCTGACCTGCTGGATT (SEQ ID NO: 3)
Reverse: CTTAGGCTTTGTATTTTGCTTTTC (SEQ ID NO: 4)

Results

This study focused on the progression of tumors and the importance of invasion during tumor-stroma interaction. Tumor cells continuously modulate the stromal microenvironment, which is important for tumor invasion [2]. Fibroblasts are basically involved in the process leading to invasion of tumor cells in the skin [1,4].

TGFβ1-Mediated Formation of Myofibroblasts

It is described that reactive oxygen species are important for many pathological processes like tumor invasion and inflammation. It is known that TGFβ1 initiates a ROS-triggered mesenchymal-mesenchymal transition (MMT) of human dermal fibroblasts to myofibroblasts [4]. Antioxidants downregulate the TGFβ1-dependent expression of αSMA. A time course analysis of TGFβ1-mediated αSMA expression in human dermal fibroblasts was performed. αSMA protein levels were measured in subconfluent fibroblast monolayer cultures in control conditioned medium ($CM^{HDF}$) or after treatment with recombinant TGFβ1 for 8 to 48 h. Treatment of HDF with recombinant TGFβ1 resulted in a significant time-dependent increase in the αSMA protein amount starting at 16 h post treatment compared with mock-treated control cells (FIG. 1A).

TGFβ1 increased the intracellular concentration of reactive oxygen species [26]. Therefore, we addressed the question of whether ROS modulate induction of αSMA. Again, a significant increase in TGFβ1-initiated αSMA protein levels was detected compared with mock-treated controls (FIG. 1B). By contrast, N-acetyl-L-cysteine and selenite either completely prevented (NAC) or significantly lowered (selenite) the TGFβ1-triggered upregulation of αSMA protein levels at 48 h after treatment with the growth factor. Incubation of HDF with the antioxidants alone did not affect αSMA expression compared with mock-treated controls (data not shown).

Antioxidants Increase Invasive Capacity of Tumor Cells

As classical antioxidants and the micronutrient selenium prevent tumor cell-mediated formation of myofibroblasts which support the invasion of tumor cells [4], the question was addressed of whether the direct treatment of tumor cells with that antioxidants affect tumor invasion. Therefore, cells of the squamous tumor cell line SCL-1 (or the melanoma cell line A375; data not shown) were incubated with antioxidants like N-acetyl-L-cysteine or selenite. The invasive capacity of treated cells and mock-treated cells was tested after a 48 h incubation period. The conditioned medium of myofibroblasts ($CM^{MF}$) resulted in a 2-fold increase in the number of invading tumor cells compared to $CM^{HDF}$-treated cells. Interestingly, the invasive capacity of SCL-1 cells was further increased by NAC and selenite. A 2.5- to 3.5-fold increase in the number of invading tumor cells was observed compared to $CM^{MF}$ (FIG. 1C). In conclusion, the antioxidant NAC and the micronutrient selenite promote tumor invasion, if the tumor cells are in direct contact with the antioxidants. Even though antioxidants are beneficial in context of prevention of myofibroblast formation, they appear to be harmful in context of tumor cell migration and invasion, respectively. As in tumor-stroma interaction in vivo the stromal cell and cancer cell are not available separately, alternative substances protecting stromal cells and preventing tumor cell invasion or even kill tumor cells would be a valuable tool for a therapeutical approach.

Characterization of $CeO_2$ Nanoparticles

Figure 2:
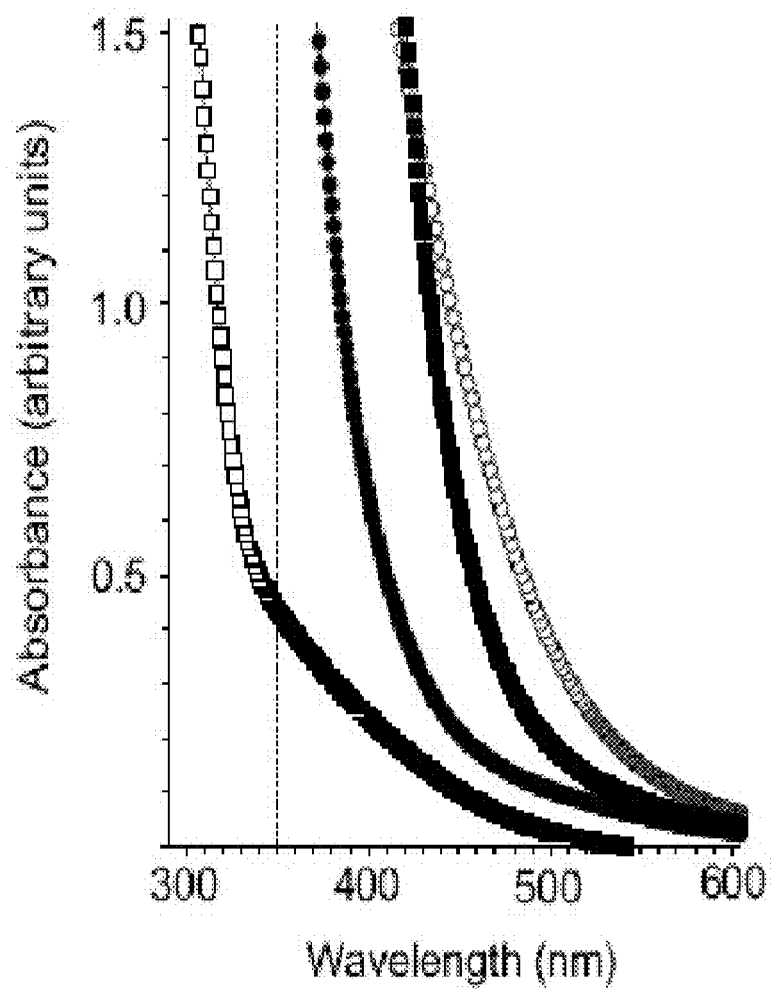
FIG. 2A shows ultraviolet-visible spectra depicting the absorbance of cerium oxide nanoparticles synthesized in water and in dextran; the absorbance edge of $Ce^{3+}$ lies between 250-350 nm while the absorbance edge of $Ce^{4+}$ lies beyond 300 nm; the absorbance of freshly synthesized CNPs in water (open circle) and the CNPs freshly synthesized in dextran (closed circle) is beyond 350 nm signifying the predominance of tetravalent oxidation state in both; slow reduction of CNPs in water is confirmed by the absorbance of CNPs below 350 nm upon aging in water for 7 days (open boxes); the aging of dextran-coated nanoparticles at neutral pH (closed boxes) does not reduce CNPs as the absorbance remains beyond 350 nm post 7 days of aging.
FIG. 2B provides HRTEM image(s) of CNPs; high resolution transmission electron micrographs of dextran stabilized cerium oxide nanoparticles: a) low magnification image depicting the distribution of nanoparticles; b) high magnification micrographs reveal the non agglomerated and uniformly dispersed 3-5 nm nanoparticles; c) and d) high magnification image depicting lattice fringes of CNPs from dispersed 3-5 nm particles.
FIG. 2C shows transmission electron microscopy (TEM) and fluorescence micrograph of $CeO_2$ nanoparticles; subconfluent fibroblasts (HDF) (a,c) and tumor cells (SCL-1) (b,d) were mock-treated or treated with 150 µM $CeO_2$/dextran for 16 h to determine the cellular uptake of nanoceria; fluorescence microscopy to study the subcellular localization of FITC-labeled CNP; human dermal fibroblasts (e) and squamous tumor cells (f) were exposed to FITC-labeled cerium oxide nanoparticles (150 µM) for 24 h and photographed thereafter.
FIG. 2D illustrates distribution of nanoceria ($CeO_2$) in murine skin; eight week CD-1 mice were treated with $CeO_2$/dextran nanoparticles and the amount of $CeO_2$ in skin measured as described in Materials and Methods; the bar graphs represent mean and s.e.m.
FIG. 2E depicts line graphs showing that CNPs with predominant Ce3+ oxidation state and dextran coated CNPs were SOD active at both neutral and acidic pH while the CNPs with predominant Ce4+ oxidation state were not SOD active.
FIG. 2F provides line graphs showing catalase activity of CNPs, which was tested using Amplex red assay (Invitrogen) as described previously (Chem Comm 2010); the nanoparticles were buffered to pH 3 and 7 to see the effect of pH change on the catalase activity of nanoparticles; as shown in this illustration; catalase activity of dextran coated nanoparticles was reduced by 40% or more in an acidic pH as compared to activity at pH 7; the same trend was observed for CNPs with predominant $Ce^{4+}$ oxidation state while CNPs with predominant $Ce^{3+}$ oxidation did not show any catalase activity.
Figure 2:
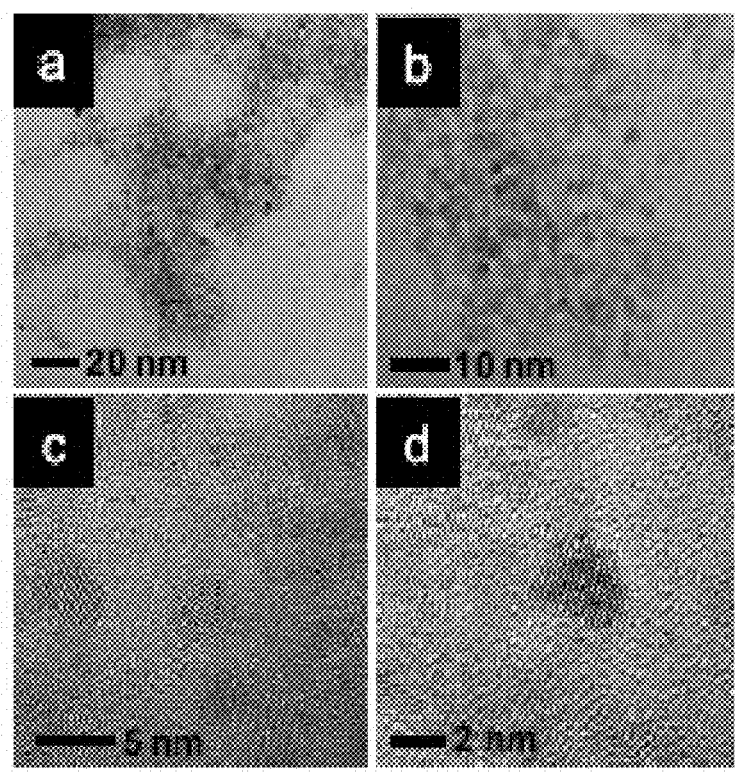
Figure 2:
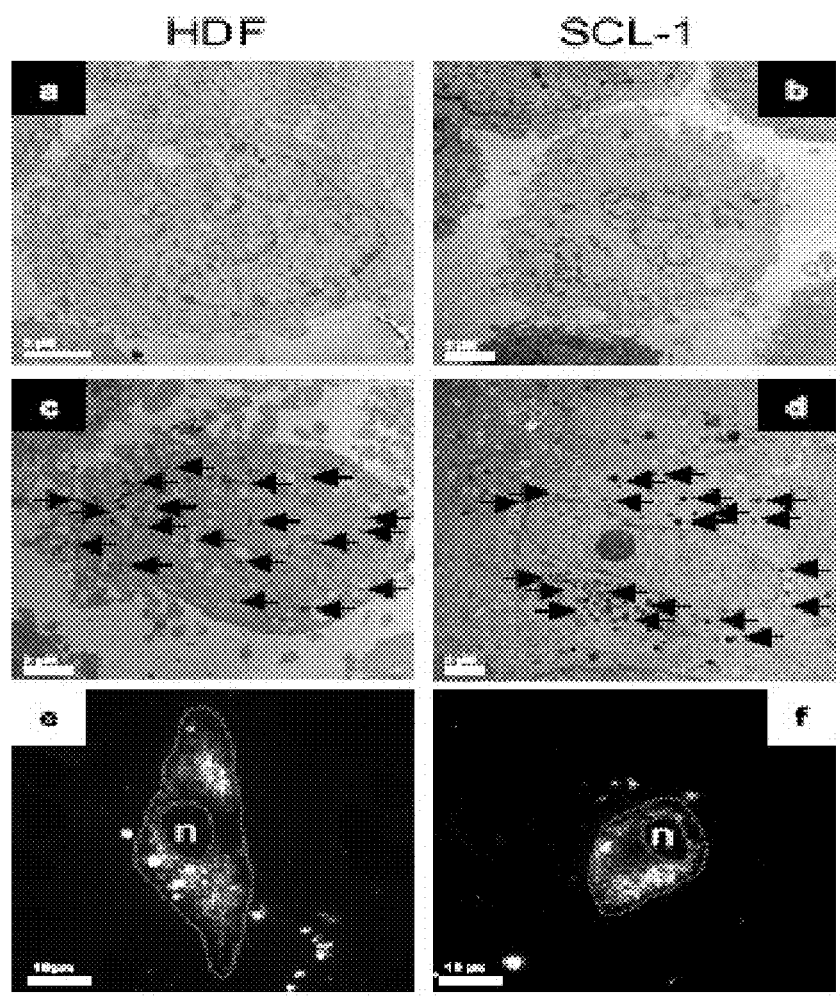
Figure 2:
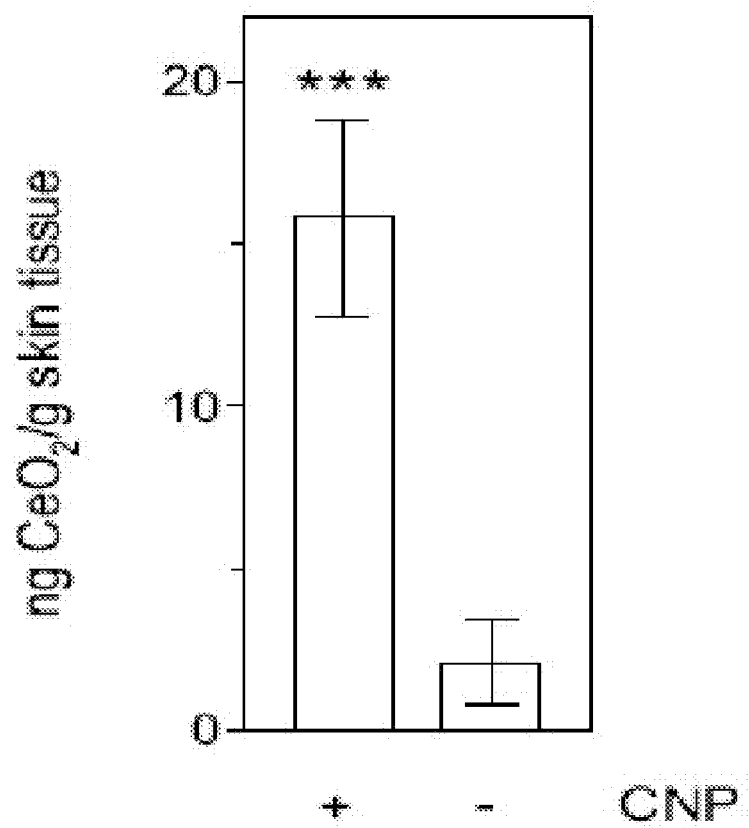
Figure 2:
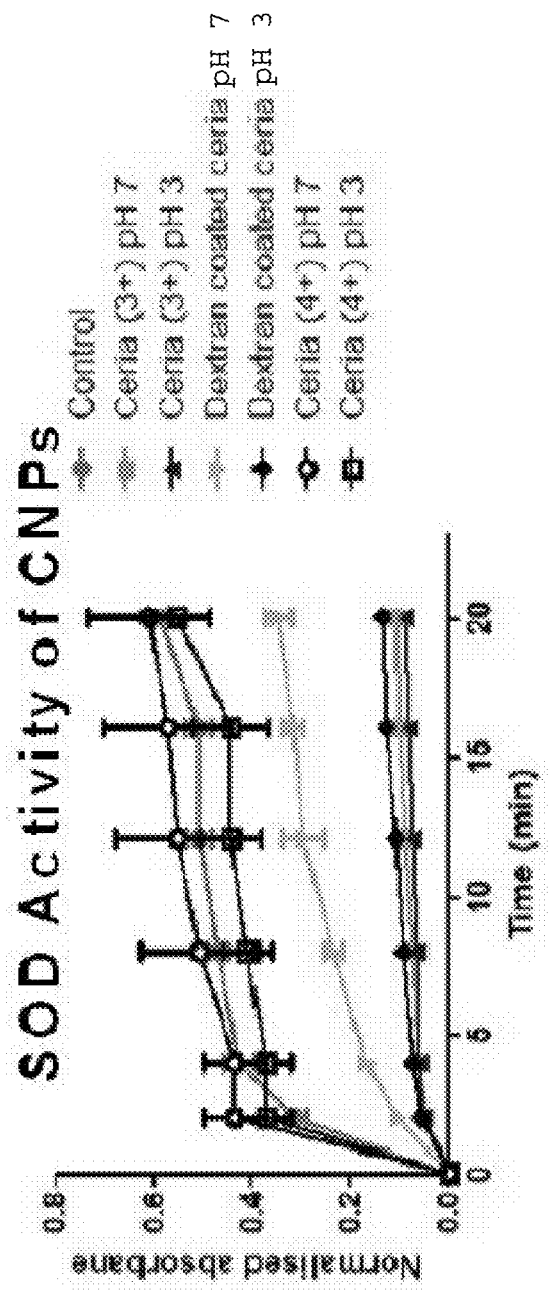
Figure 2:
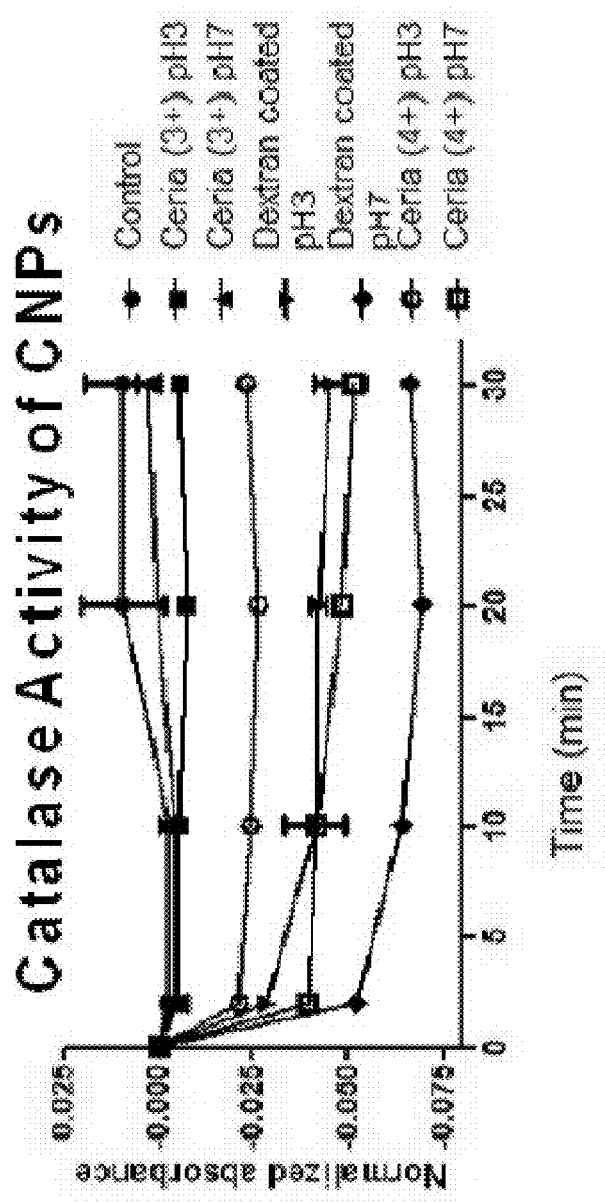

As cerium oxide based nanoparticles (CNP) have been shown to have prooxidant or antioxidant activity depending on the environmental pH [27], the effect of CNP on stromal and tumor cells was investigated herein. The absorbance edge of $Ce^{3+}$ lies between 250-350 nm while the absorbance edge of $Ce^{4+}$ lies beyond 350 nm. The absorbance of freshly synthesized CNP in water (open circle) and in dextran (closed circle) is beyond 350 nm indicating the predominance of tetravalent oxidation state ($Ce^{4+}$) in both preparations (FIG. 2A). Slow reduction of CNP in water (open boxes) is confirmed by the absorbance of CNP below 350 nm (dotted line) upon aging in water for 7 d reflecting a change in the ratio of $Ce^{3+}/Ce^{4+}$ towards $Ce^{3+}$. The aging of nanoparticles in dextran does not reduce CNP as the absorbance remains beyond 350 nm post 7 d of aging (closed boxes), indicating a stable $Ce^{3+}/Ce^{4+}$ ratio at neutral pH. Therefore, for further studies the stable dextran-coated cerium oxide nanoparticles were used.

FIG. 2B shows a representative low magnification image depicting the distribution of nanoparticles (a). The high magnification micrographs reveal the non agglomerated and uniformly dispersed 3-5 nm nanoparticles (b) while (c) and (d) depict the high magnification lattices from dispersed 3-5 nm CNP.

Superoxide Dismutase and Catalase Activity of Cerium Oxide Nanoparticles

The SOD mimetic activity of CNPs was tested as described previously (Chem Comm 2007, Biomaterials 2008). In addition the nanoparticles were buffered to pH 3 and 7 to determine the effect of change in pH on the SOD activity of nanoparticles. Three different sets of nanoparticles were tested: viz. CNPs with predominant $Ce^{3+}$ oxidation state, with predominant $Ce^{4+}$ oxidation state and dextran-coated nanoparticles (mixed oxidation state). It can be observed from FIG. 2E that CNPs with predominant $Ce^{3+}$ oxidation state and dextran coated CNPs were SOD active at both neutral and acidic pH while the CNPs with predominant $Ce^{4+}$ oxidation state were not SOD active.

The catalase activity of CNPs was tested using Amplex red assay (Invitrogen) as described previously (Chem Comm 2010). Additionally the nanoparticles were buffered to pH 3 and 7 to observe any effect in the catalase activity of nanoparticles. As seen from FIG. 2F the catalase activity of dextran coated nanoparticles was reduced by 40% or more in acidic pH as compared to the activity at pH 7. The same trend was observed for CNPs with predominant $Ce^{4+}$ oxidation state while CNPs with predominant $Ce^{3+}$ oxidation did not show any catalase activity consistent with our previously obtained results (Chem Comm 2007, Chem Comm 2010 and Biomaterials 2008).

CNP Distribution in Cell Culture and In Vivo

Transmission electron microscopy (TEM) was used to follow the cellular uptake of CNP. The TEM micrographs of human dermal fibroblasts (a, c) and SCL-1 tumor cells (b, d) show an uptake of the $CeO_2$ nanoparticles at 16 h upon treatment (c, d) compared to mock-treated controls (a, b) (FIG. 2C). However, the size of the incorporated CNP was measured to be 50 nm based on the scale of the micrographs. As the size of the added CNP primarily was about 5 nm (FIG. 28), the nanoparticles at least in part agglomerated in the cells. CNP smaller than 50 nm could not be seen under commonly used experimental conditions. In order to follow more precisely the distribution of the intracellular particles, fluorescent dye-labeled CNP were used. After incubation of fibroblasts and tumor cells with fluorescein-isothiocyanate (FITC)-labeled CNP, a broad fluorescent staining of the cells was observed. The CNP were ubiquitously distributed in the cytosol (FIG. 2C; E, F). To ensure that the FITC fluorescence really reflected incorporated CNP and was not due to absorption on the cell surface, the cells were washed and passaged. The nanoparticles were still detectable (data not shown).

In another set of experiments the distribution of cerium oxide nanoparticles in the skin of a murine model was established. FIG. 2D shows an increased $CeO_2$ amount in the skin of the mice after six weeks of supplementation. In comparison to mock-treated mice, an up to 8-fold increase in the amount of $CeO_2$ per gram skin tissue was detected in CNP-treated mice.

Results

Cytotoxicity of Cerium Oxide Nanoparticles on Fibroblasts

Figure 3:
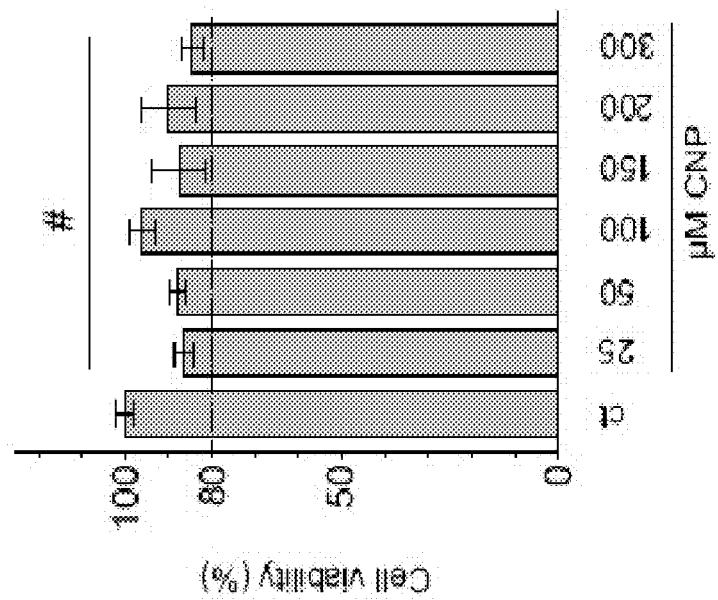
FIG. 3A depicts cytotoxicity of $CeO_2$ on fibroblasts; subconfluent human dermal fibroblasts were treated with different concentrations of CNP; the percentage of living cells was measured after 48 h; three independent experiments were performed.
FIG. 3B shows that nanoceria particles downregulate TGFβ1-mediated mRNA expression of αSMA; total RNA was isolated from cells cultured in $CM^{HDF}$ and either untreated or pretreated for 24 h with 50 µm or 150 µM $CeO_2$/dextran before addition of rTGFβ1 (5 ng/ml); TGFβ1 and the cerium oxide particles were present for an additional 48 h; mRNA copy numbers were determined by quantitative real-time RT-PCR; values are given as ratios of target gene mRNA copy number compared to the housekeeping gene HPRT1 and represent means±s.e.m. from three independent experiments; CM, conditioned medium.
FIG. 3C indicates that αSMA expression in human dermal fibroblasts is inhibited by CNP; subconfluent HDF were cultured in $CM^{HDF}$ and either mock-treated or pretreated for 24 or 48 h with 150 µM $CeO_2$/dextran before addition of rTGFβ1 (5 ng/ml); TGFβ1 and the cerium oxide particles were present for an additional 48 h.; α-tubulin was used as loading control; three independent experiments were performed; CM, conditioned medium.
FIG. 3D shows that CNP inhibit TGFβ1-mediated transdifferentiation in collagen lattices; fibroblasts seeded for 2 d in the dermal equivalent (DE) were mock-treated or treated with 150 µM CNP prior to stimulation with rTGFβ1 (5 ng/ml); the diameter (in cm) of the contracted or non-contracted collagen lattices was used as a measure of the contractile force of the cells; three independent experiments were performed; bar equals 1 cm.
FIG. 3E depicts that CNPs downregulate TGFβ1-mediated mRNA expression of αSMA in dermal equivalents; dermal equivalents were incubated for 2 d with rTGFβ1 (5 ng/ml) or in combination with 150 µM CNP; after collagenase treatment, the dermis was homogenized and 50 µl clear lysate was subjected to western blot analysis for αSMA; α-tubulin was used as a loading control; two independent experiments were performed; cc-GAG, collagen-chitosan-glycosaminoglycan; d, dermis; f, fibroblasts; k, Bar, 25 µm.
Figure 3:
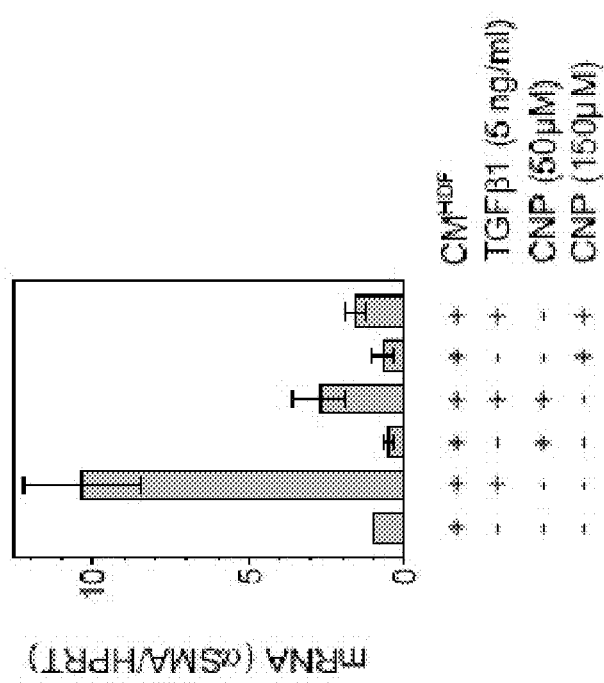
Figure 3:
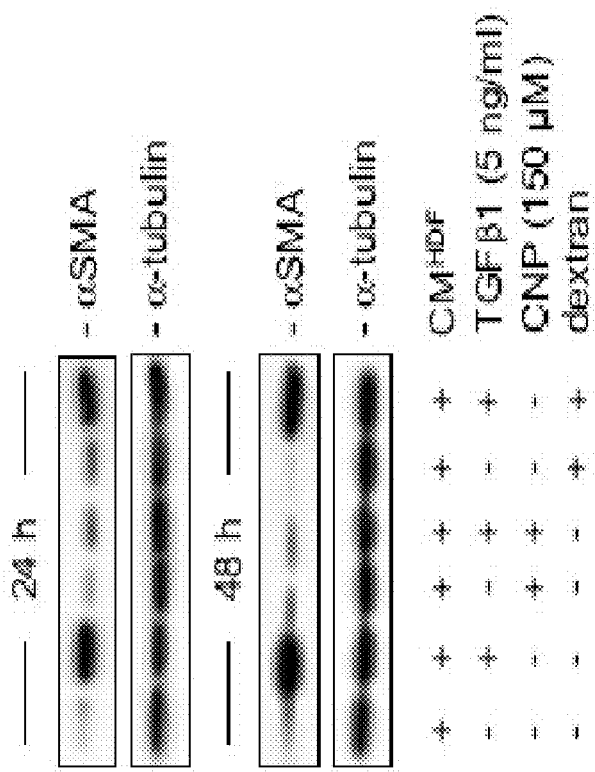
Figure 3:
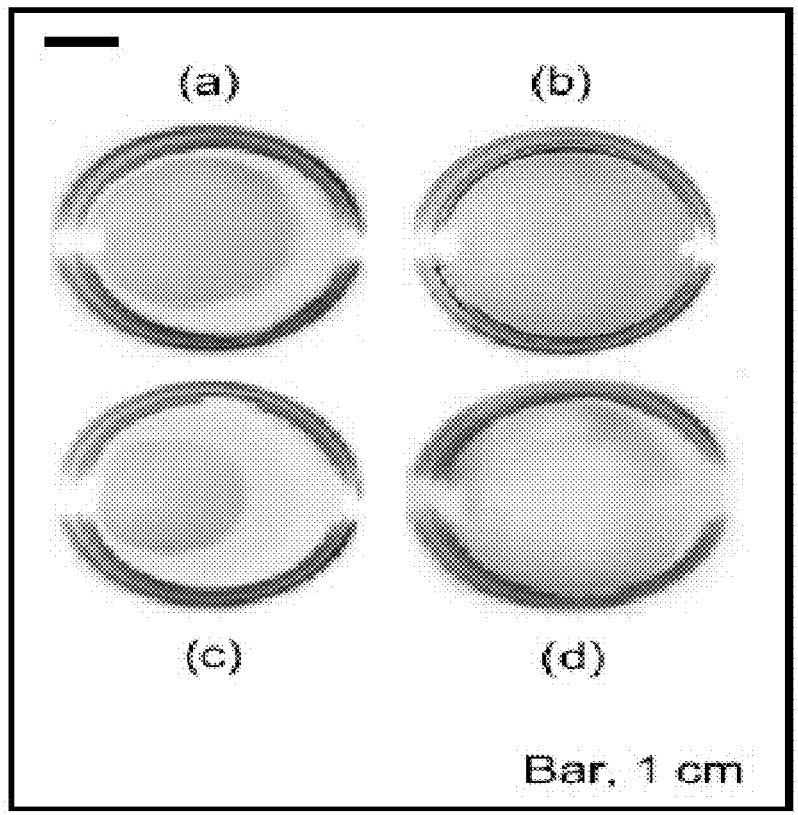
Figure 3:
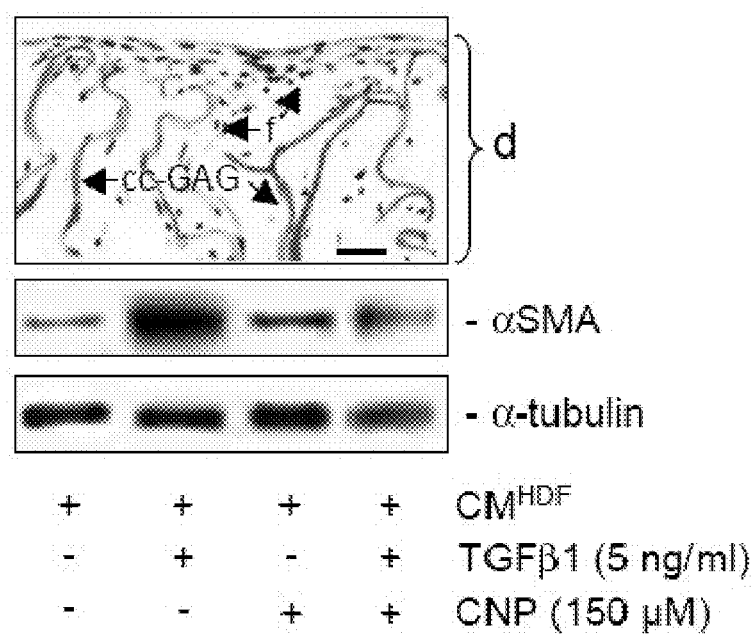

Recent studies deal with a free radical scavenging mechanism of CNP in mammalian cells. $CeO_2$ particles of less than 20 nm have been shown to increase cellular survival [28]. Herein, the MTT assay was used to determine optimal concentrations at which more than 80% of dermal fibroblasts survived at least 48 h after incubation with no change in morphology. Concentrations up to 300 μM did not show any cytotoxic effect at 48 h after CNP incubation (FIG. 3A). No change in morphology was observed (data not shown). Compared to mock-treated cells, significant toxicity of the $CeO_2$ particles was not detected ($p<0.5$, ANOVA).

Cerium Oxide Nanoparticles Prevent Myofibroblast Formation.

It has previously been suggested that $CeO_2$ nanoparticles may exert cytoprotective effects based on the chemical properties of that material [29-31]. we performed real-time RT-PCR to study the effect of CNP on levels of αSMA mRNA in human dermal fibroblasts. The 'housekeeping' gene HPRT was used as internal control. TGFβ1 caused a 10-fold increase in αSMA steady-state mRNA levels at 24 h after treatment compared to mock-treated controls. Preincubation with non-toxic concentrations of CNP significantly counteracted the TGFβ1-initiated transcription of αSMA mRNA (FIG. 3B). These data correlated with the αSMA protein amount (FIG. 3C). The increase in the TGFβ1-triggered αSMA protein levels at 24 or 48 h upon treatment was almost completely abrogated by the application of CNP compared to TGFβ1 or TGFβ1 plus dextran treated cells (FIG. 3C).

Three-dimensional free-floating collagen gels [32,33] were used to exclude an artificial effect of TGFβ1 and CNP due to cells in monolayer cultures. Cells in that mechanically released lattices were allowed to contract them. The occurrence of myofibroblasts is characterized by their capability to contract the free-floating collagen gel (FIG. 3D). A decrease in the area and diameter of the collagen gel is inversely proportional to the increase in the number of myofibroblasts [34,35]. Compared to the collagen lattices of untreated (a) or CNP-treated fibroblasts (b), the diameter of the lattices treated with TGFβ1 (c) was significantly lowered after 4 d of contraction, reflecting the existence of myofibroblasts. Treatment of the fibroblasts located in the collagen gels with CNP prior to TGFβ1 application (d) resulted in a marginal contraction of the collagen lattices compared to untreated controls, which corresponded with a significantly lowered expression of αSMA.

These data were confirmed by preincubation of the fibroblasts with CNP in a 3-dimensional dermal equivalent (DE) [26] (FIG. 3E). The contraction in that model is prohibited by the used extracellular matrix. Therefore, the DE resembles the dermis under physiological conditions in vivo. Normal human skin characteristics were apparent in paraffin sections of dermal equivalents stained with hematoxylin-eosin (HE) (FIG. 3E), which is in line with previously published data [26]. Treatment of fibroblasts with TGFβ1 in conditioned medium (CMHDF) resulted in a significant increase in αSMA protein levels compared to mock-treated cells (FIG. 3E). Furthermore, the DE was incubated with CNP prior to TGFβ1 treatment. CNP prevented the increase in αSMA protein amount by about 60%. The data obtained with the dermis equivalents agree with data from the monolayer cell cultures, indicating the prevention of TGFβ1-mediated fibroblast to myofibroblast transition by CNP in a more complex system resembling the human dermis.

Oxidation of Proteins by TGFβ1-Mediated Reactive Oxygen Species

Figure 4:
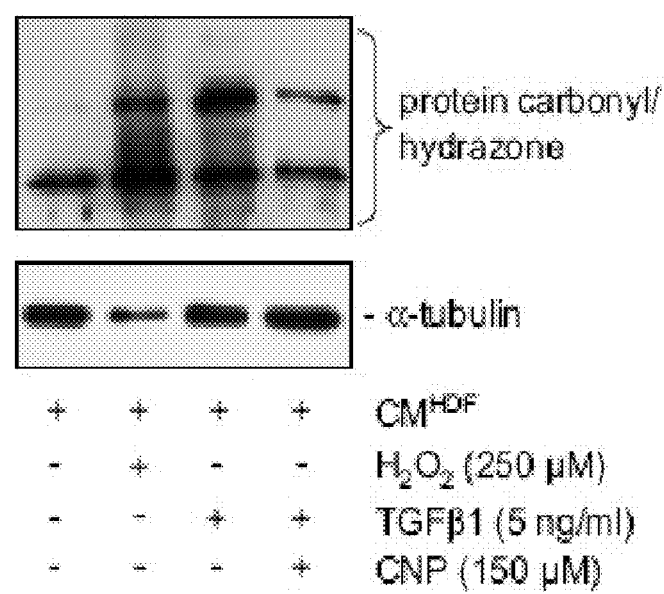
FIG. 4 shows oxidation of target structures; subconfluent HDF were cultured in $CM^{HDF}$ and either mock-treated or pretreated for 40 h with 150 µM $CeO_2$/dextran before addition of rTGFβ1 (5 ng/ml); TGFβ1 and the CNPs were present for an additional 8 h; $H_2O_2$ was used as positive control at a concentration of 250 µM for 1 h; the level of protein oxidation was determined by western blot analysis; α-tubulin was used as loading control; three independent experiments were performed.

ROS can directly generate damage in DNA, lipids and proteins. As TGFβ1 initiates the reactive oxygen species-dependend expression of αSMA [4], the effect of CNP on ROS production was studied. An increase in the concentration of intracellular ROS leads to oxidized (carbonylated) proteins, a hallmark of oxidative stress [36]. The question was addressed of whether CNP prevent TGFβ1-mediated production of ROS and consequently avoid the oxidation of proteins. In mock-treated fibroblasts ($CM^{HDF}$) a low amount of oxidized proteins was detected whereas in TGFβ1-treated cells the amount of oxidized proteins was significantly increased (FIG. 4). Treatment of CNP significantly lowered the TGFβ1-mediated protein oxidation. Hydrogen peroxide was used as positive control (FIG. 4).

Cytotoxicity of Cerium Oxide Nanoparticles on Squamous Tumor Cells

As tumor progression is associated with activation of the stroma via molecular crosstalk between tumor cells and stromal cells, we studied the effect of CNP on the squamous tumor cell line SCL-1. The MTT assay was used to determine concentrations at which SCL-1 tumor cells show cytotoxicity. FIG. 5A shows the viability of the SCL-1 cells after incubation with different concentrations of CNP after 48 h. Treatment of the tumor cells with CNP at a concentration of 150 µM, resulting in no loss of viability of dermal fibroblasts (see FIG. 3A), led to a significant toxicity for tumor cells. More than 50% of the tumor cells were sensitive to cell killing at that concentration (FIG. 5A). Similar data were obtained by A375 melanoma cells (data not shown). A concentration of 250 µM CeO2 nanoparticles did not increase the cytotoxicity at 48 h post treatment. However, a fraction of 50% of the tumor cells still survived at that experimental conditions. These cells were used for invasion studies.

Involvement of CNP in Tumor Invasion

Prevention of transdifferentiation by antioxidants inhibits the myofibroblast-mediated increase in tumor invasion [4]. Myofibroblasts were found at the invasion front of some tumors [37], suggesting that myofibroblasts are involved in processes of tumor invasion and metastasis. In this study we tested whether the invasive capacity of tumor cells may be modulated by CNP-dependent inhibition of myofibroblast formation. The formation of myofibroblasts was prevented by treatment of subconfluent HDF cultures in $CM^{HDF,TGF}$ with CNP. After treatment of HDF with different concentrations of CNP and TGFβ1, the medium was replaced by serum-free DMEM for an additional 48 hours. These media ($CM^{HDF,TGF,CNP}$) were used for invasion assays (FIG. 5B). Compared with the medium from mock-treated cells ($CM^{HDF}$) conditioned medium from myofibroblasts ($CM^{HDF,TGF}$) led to a 2.2-fold increase in the invasive capacity of SCL-1 tumor cells. $CM^{HDF,TGF,CNP}$ resulted in a 70% lowered invasive capacity of the squamous tumor cells compared with $CM^{HDF,TGF}$, suggesting that CNP play a role in lowering the invasive capacity of tumor cells.

Figure 5:
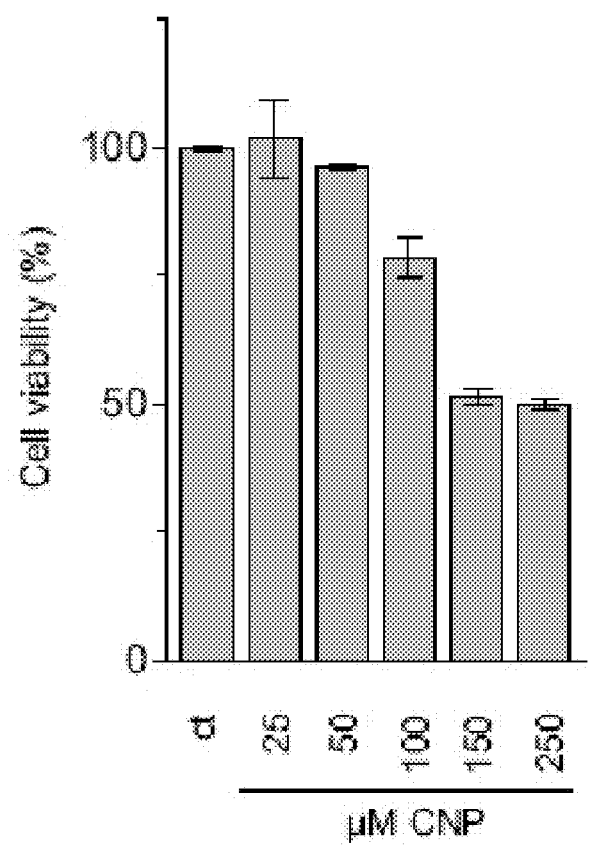
FIG. 5A illustrates cytotoxicity of $CeO_2$ on squamous tumor cells; subconfluent squamous tumor cells (SCL-1) were treated with different concentrations of $CeO_2$/dextran (CNP); the percentage of living cells after 48 h was measured; the experiments were performed in three independent experiments; Ct, control (mock-treated)
FIG. 5B shows CNP-mediated inhibition of myofibroblast formation results in downregulation of tumor invasion; conditioned media of HDF ($CM^{HDF}$), myofibroblasts ($CM^{MF}$) and cells treated with rTGFβ1 and CNP $CM^{HDF,TGF,CNP}$) were used for the invasion assays based on matrigel-coated transwells; the total number of tumor cells migrating towards the chemoattractive media over a 48 h time period is a measure of the invasive capacity; the data represent the mean±s.e.m. of three independent experiments; **P<0.01 versus CMMF (ANOVA, Dunnett's test)
FIG. 5C presents the lowered invasive capacity of CNP-loaded tumor cells; subconfluent SCL-1 tumor cells were cultured in $CM^{HDF}$ and either mock-treated or pretreated for 24 h with 50 μM or 150 μM $CeO_2$; the invasive capacity of these cells was tested with conditioned media of HDF ($CM^{HDF}$) and myofibroblasts ($CM^{MF}$); the total number of tumor cells migrating towards the chemoattractive media over a 48 h time period is a measure of the invasive capacity; the data represent the mean±s.e.m. of three independent experiments; **P<0.1 versus CMMF (ANOVA, Dunnett's test). CM, conditioned medium.
Figure 5:
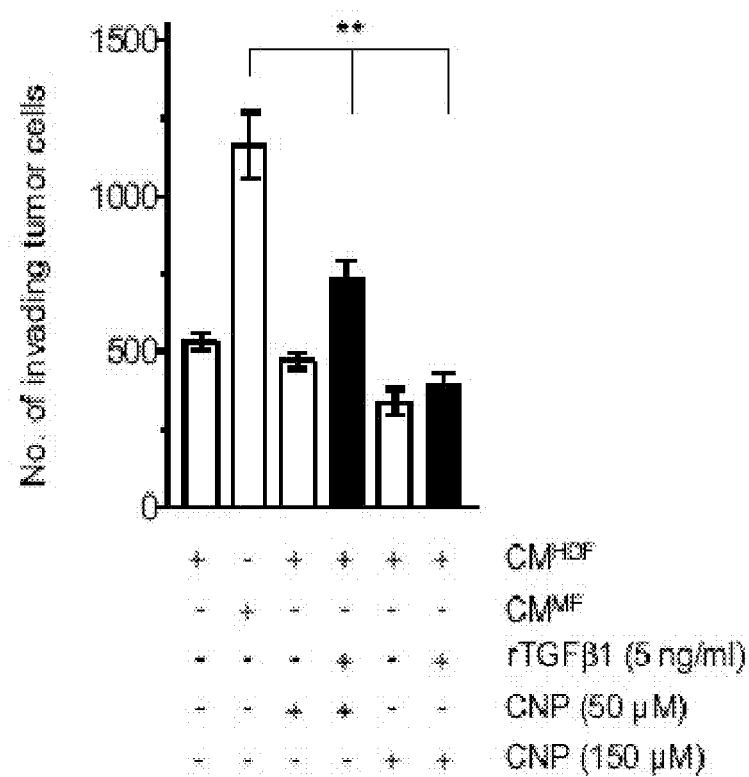
Figure 5:
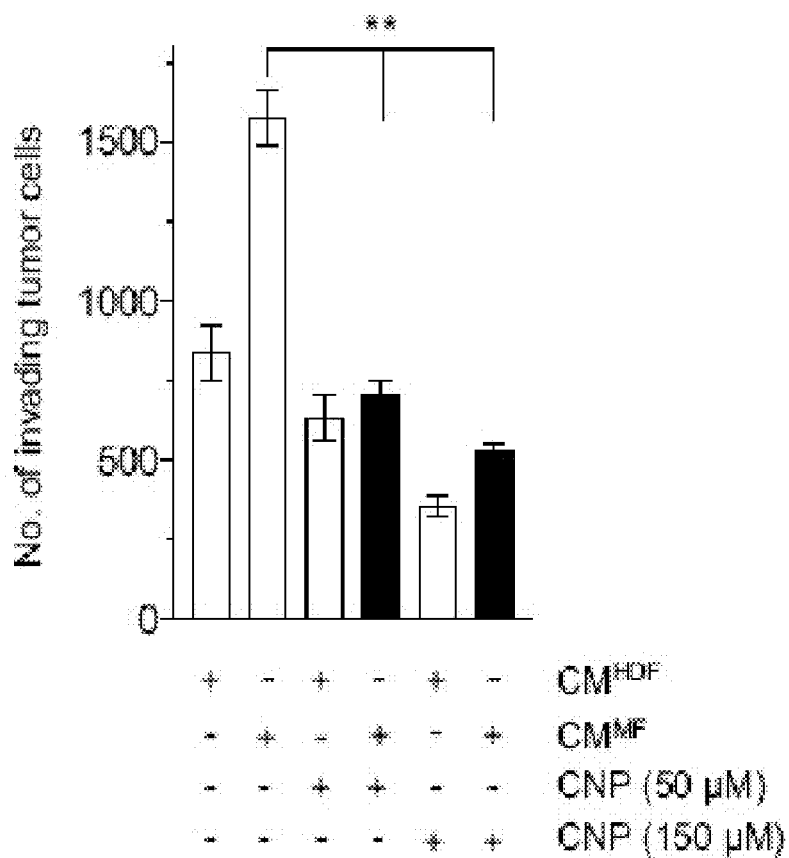

Furthermore, the question was addressed whether the direct treatment of tumor cells with CNP affects tumor invasion. Therefore, squamous tumor cells SCL-1 were incubated with different concentrations of CNPs. Forty-eight hafter treatment the invasive capacity of these SCL-1 cells and mock-treated control cells were tested with conditioned media from HDF ($CM^{HDF}$) and from myofibroblasts ($CM^{MF}$) (FIG. 5 C). The invasive capacity of tumor cells is modulated by CNPs. Compared to mock-treated cells, the invasive capacity of CNP-preincubated SCL-1 cells was significantly lowered. In conclusion, CNP inhibit tumor invasion, if either the tumor cells are in direct contact with the nanoparticles (FIG. 5C) or the formation of myofibroblasts is prevented by CNP (FIG. 5B).

Oxidation of Proteins by CNP-Initiated Reactive Oxygen Species in Tumor Cells.

Figure 6:
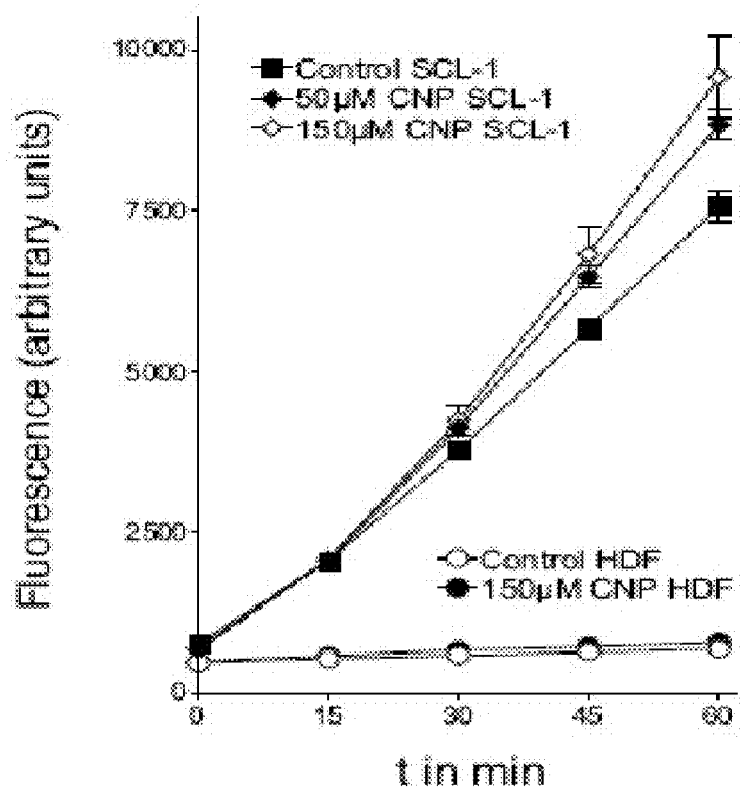
FIG. 6A depicts that nanoceria increase the level of reactive oxygen species (ROS) in tumor cells; subconfluent SCL-1 and HDF were preincubated with 50 μM and 150 μM $CeO_2$/dextran for 24 h in $CM^{SCL-1}$ or $CM^{HDF}$; increase of DCF fluorescence as a measure of increase in ROS was followed over 60 minutes versus untreated controls; the experiments were performed in triplicate; CM, conditioned medium.
FIG. 6B shows oxidation of target structures; subconfluent SCL-1 cells were cultured in $CM^{SCL-1}$ and either mock-treated or treated for 16 h with 150 μM $CeO_2$/dextran before oxidized proteins were determined by western blot analysis; $H_2O_2$ was used as positive control at a concentration of 250 μM for 1 h.; α-tubulin was used as loading control; three independent experiments were performed; CM, conditioned medium.
FIG. 6C shows expression of HIF-1 in human dermal fibroblasts HDF and squamous tumor cells SCL-1; representative Western blot demonstrates HIF-1α protein expression in HDF and SCL-1 cells either mock-treated or treated with 100 μM cobalt chloride for 4 h.; α-tubulin was used as loading control; two independent experiments were performed; CM, conditioned medium.
Figure 6:
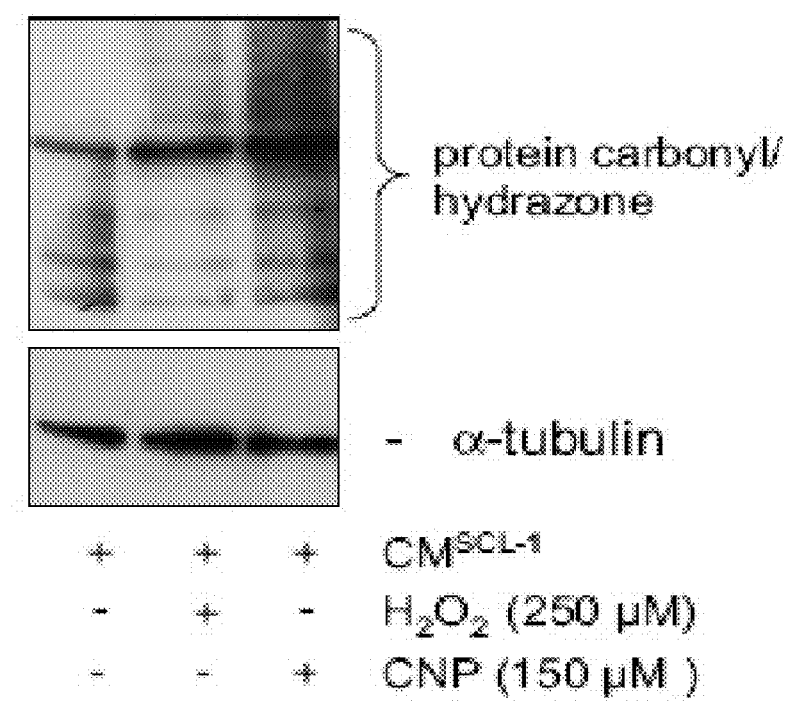
Figure 6:
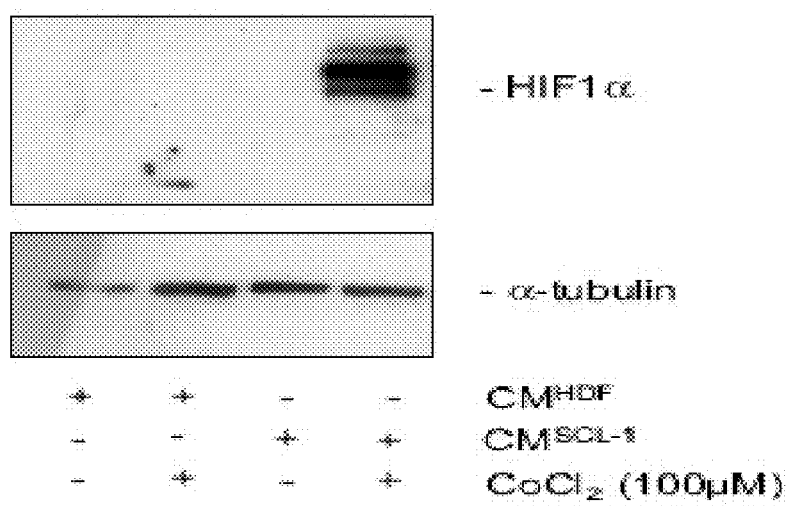

As a modulation of intracellular ROS levels by nanoparticles is suggested, we studied the effect of CNP on ROS production in the squamous SCL-1 cell line and human dermal fibroblasts (HDF). Therefore, time-course analysis of ROS generation after treatment with CNP of subconfluent HDF or SCL-1 cells was performed (FIG. 6A). Incubation of the tumor cells with CNP resulted in a significant increase in dichlorofluorescein (DCF) staining compared to mock-treated cells which was maintained over the studied time range. This suggests that CNP increases intracellular ROS level in SCL-1 cells. By contrast, no increase in ROS levels was measured in HDF after CNP treatment compared to untreated controls. Interestingly, the mock-treated HDF had a significant lower level of intracellular ROS compared to mock-treated SCL-1 tumor cells. A non-toxic concentration of 250 µM H$_2$O$_2$ which was used as technical control, further increased the intracellular ROS level (data not shown). Furthermore, a CNP-initiated and ROS-mediated oxidation of proteins was studied. Indeed, the amount of oxidized proteins was significantly increased in CNP-treated cells (FIG. 6B) compared to mock-treated SCL-1 cells. Hydrogen peroxide was used as positive control resulting in an increase in oxidized proteins. These data support the hypothesis that CNP has a prooxidant effect in tumor cells.

Accumulation of Hypoxia-Inducible Factor 1 (HIF-1)

Hypoxia-inducible factor 1 (HIF-1) is a heterodimeric transcription factor playing a critical role in tumor cells [38]. HIF-1 is highly expressed in tumor cells but having a high turnover rate as well. The factor is rapidly degraded by the proteasomal pathway. Hypoxic conditions or chemical inhibitors of the hydroxylases, such as cobalt, inhibit HIF-1 degradation and stabilize its expression. Treatment of SCL-1 cells with a non-toxic concentration of 100 µM cobalt chloride for 4 h resulted in a significant increase in HIF-1 protein levels compared to mock-treated cells (FIG. 6C). HDF showed no HIF-1 protein expression and were not affected by cobalt chloride.

Discussion

With the rapidly increasing number of publications on the health effects of nanomaterials, nanoparticles have drawn attention to their potential harmful effects [39]. The unique properties of these materials such as large specific area and greater reactivity resulted in questions regarding potential toxicological effects [40]. Even though the potential cytotoxic effects of nanoparticles on human health are controversially discussed, a few preliminary studies have demonstrated toxic effects [41,42]. On the other hand, some types of nanoparticles, for example cerium oxide based nanoparticles (CNP, nanoceria), seem to have more beneficial effects. Due to the valence and oxygen defect properties and their unique ability to switch oxidation states between III (Ce$^{3+}$) and IV (Ce$^{4+}$), CNP are described to have antioxidant activity [12,43]. As other data postulate a prooxidant mechanism of CNP in human cells depending on the structure as well as exogenous and endogenous conditions [11,44], the question was addressed in our study of whether that discussed bifunctional character may be used as a therapeutical tool in tumor-stroma interaction. In skin cancer, tumor cells interact with their cellular microenvironment, such as (stromal) fibroblasts [1,2,4]. The data herein showed that non-toxic concentrations of dextran-coated CNP with a size of 3-5 nm in diameter prevent the TGF 1-initiated and ROS-triggered expression of αSMA, a biomarker of myofibroblasts. Furthermore, the invasive capacity of tumor cells was dramatically lowered by inhibition of myofibroblast formation via CNP. That finding is in line with the prevention of myofibroblast formation by classical antioxidants and subsequent inhibition of tumor invasion [4,37]. Therefore, our data indicate an antioxidant mechanism of CNP in fibroblasts which is underlined by a CNP-dependent lowering of oxidized proteins. As TGF 1 increases the intracellular superoxide (O$^{2-}$) level [4,14] and CNP exerts a superoxide dismutase (SOD) mimetic activity under a neutral pH, the conclusion seems likely that the ROS-triggered formation of myofibroblasts is inhibited by CNP. In that context, the intracellular production of O$^{2-}$ by incubation of dermal fibroblasts with the redox cycling agent paraquat (Pe) was prevented by pretreatment of the cells with CNP (data not shown). Recently, it was shown that CNP with a size >300 nm in diameter and a >10-fold higher concentration induced ROS-dependent DNA damage towards human dermal fibroblasts in vitro [44]. In conclusion, a non-toxic and even protective antioxidant effect of CNP from the dominating influence of tumor cell-derived soluble factors (e.g. TGF 1) depends on particle size, concentration, and oxidation state. The oxidation state IV was demonstrated to detoxify O$^{2-}$ [43,45] resulting in a shift of the Ce$^{3+}$/Ce$^{4+}$-ratio towards oxidation state III.

In this study, the direct treatment of tumor cells with concentrations of CNP which are non-toxic for (stromal) fibroblasts increased the intracellular ROS level leading to cellular toxicity and lowered invasive capacity. The elevated amount of ROS is mediated by the mixed valence states of Ce$^{3+}$ and Ce$^{4+}$ on the surface of the nanoceria and depends on the pH value. Earlier published data [27, 46] convincingly showed that the cerium oxide nanoparticles trigger a Fenton-like reaction, if O$^{2-}$ or H$_2$O$_2$ are available which was described for tumor cells [7, 38] and showed herein. As a result, more aggressive ROS types such as hydroxyl (HO.) and hydroperoxyl (HO$_2$.) radicals are generated which damage the cells. The autocatalytic and autoregenerative capacity of CNP (Ce$^{3+}$ ⇒ Ce$^{4+}$ ⇒ Ce$^{3+}$) given under physiological pH conditions is abrogated under an acidic pH. Here, the ratio of Ce$^{3+}$/Ce$^{4+}$ is rapidly shifted to an irreversible higher concentration of Ce$^{3+}$. Transmittance curves underline that hypothesis [46]. As a result, less Ce$^{4+}$ is available per time for a potential antioxidant and detoxifying reaction and a prooxidant reaction is boosted in tumor cells.

What is the reason for a lowered pH in tumor cells? More than 50 years ago, the Nobel prize laureate Otto Warburg described that cancer cells greedily consume glucose and produce lactic acid even under aerobic conditions resulting in an acidic cytosolic pH. This phenomenon is called the 'Warburg effect' [47,48]. Recently, the Warburg effect, which is part of the concept of metabolic remodelling in tumor cells, returns to the cancer stage [49, 50]. A continuously elevated concentration of reactive oxygen species in tumor cells (see FIG. 6) may be the trigger for HIF1α expression and stabilization. HIF1α was recently described as key regulator of the metabolic remodelling resulting, for example resulting in enhanced glycolysis and lactate production [38,50]. An elevated HIF1α level was detected in our study herein which fits to earlier published data and may explain the prooxidant mechanism of CNP in tumor cells.

In summary, this study is the first to show that cerium oxide nanoparticles have a dual function in tumor-stroma interaction, namely beneficial for stromal cells and harmful for tumor cells, based on the Warburg effect. Nanoceria reveal an inhibitory effect on the formation of myofibroblasts. Furthermore, concentrations of cerium oxide being non-toxic on normal (stromal) cells (e.g. fibroblasts) showed an inhibitory, even ROS-dependent cytotoxic and anti-invasive effect on squamous tumor cells. The understanding of the interaction between tumor cells, its surrounding stroma and engineered nanoparticles could result in novel therapeutic strategies to combat metastatic spread more efficiently in the future.

Accordingly, in the drawings and the above specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES CITED

[1] de Wever, O. & Mareel, M. Role of tissue stroma in cancer cell invasion. J. Pathol. 200, 429-447 (2003).
[2] Liotta, L. A. & Kohn, E. C. The microenvironment of the tumour-host interface. Nature 411, 375-379 (2001).
[3] Pupa, S. M. et al. New insights into the role of extracellular matrix during tumor onset and progression. J. Cell. Physiol. 192, 259-267 (2002).
[4] Cat, B, et al. Enhancement of tumor invasion depends on transdifferentiation of skin fibroblasts mediated by reactive oxygen species. J. Cell Sci. 119, 2727-2738 (2006).
[5] Kunz-Schughart, L. A. Knuechel R. Tumor-associated fibroblasts (part II): functional impact on tumor tissue. Histol. Histopathol. 17, 623-637 (2002).
[6] Desmouliere, A. et al. The stroma reaction myofibroblast: a key player in the control of tumor cell behavior. Int. J. Dev. Biol. 48: 509-517 (2004).
[7] Cerutti, P. et al. The role of the cellular antioxidant defense in oxidant carcinogenesis. Environ. Health Perspect. 102, 123-129 (1994).
[8] Freitas, R. A. What is nanomedicine? Nanomedicine 1, 2-9 (2005)
[9] Barry, S. E. Challenges in the development of magnetic particles for therapeutic applications. Int. J. Hyperth. 24, 451-466 (2008).
[10] Corchero, J. L. Villaverde, A. (2009) Biomedical applications of distally controlled magnetic nanoparticles. Trends Biotechnol. 27, 468-476 (2009).
[11] Lin, W. et al. Toxicity of Cerium Oxide Nanoparticles in Human Lung Cancer Cells. Int. J. of Toxicol. 25, 451-457 (2006).
[12] Karakoti, A. S. et al. Nanoceria as Antioxidant: Synthesis and Biomedical Applications. JOM 60, 33-37 (2008).
[13] Karakoti, A. S. et al. PEGylated Nanoceria as Radical Scavenger with Tunable Redox Chemistry. J. Am. Chem. Soc. 131, 14144-14145 (2009).
[14] Thannickal, V. J. Fanburg, B. L. Reactive oxygen species in cell signaling. Am. J. Physiol. Lung Cell Mol. Physiol. 279, L1005-L1028 (2000).
[15] Bayreuther K. et al. Terminal differentiation, aging, apoptosis, and spontaneous transformation in fibroblast stem cell systems in vivo and in vitro. Ann. N. Y. Acad. Sci. 663, 167-179 (1992).
[16] Boukamp, P. et al. Phenotypic and genotypic characteristics of a cell line from a squamous cell carcinoma of human skin. J. Natl. Cancer Inst. 68, 415-427 (1982).
[17] Stuhlmann, D. et al. Modulation of homologous gap junctional intercellular communication of human dermal fibroblasts via a paracrine factors generated by squamous tumor cells. Carcinogenesis 24, 1737-1748 (2003).
[18] Reynolds, E. S. The use of lead citrate at high pH as electron opaque stain in electron microscopy. J. Cell Biol. 17, 208-212 (1963).
[19] MoαSMAnn, T. Rapid colorimetric assay for cellular growth and survival: application to proliferation and cytotoxicity assays. J. Immunol. Methods 65, 55-63 (1983).
[20] Speckmann, B. et al. Selenoprotein P expression is controlled through interaction of the coactivator PGC-1alpha with FoxO1a and hepatocyte nuclear factor 4alpha transcription factors. Hepatology 48, 1998-2006 (2008).
[21] Nishimura, M. et al. Effects of prototypical drug-metabolizing enzyme inducers on mRNA expression of housekeeping genes in primary cultures of human and rat hepatocytes. Biochem. Biophys. Res. Commun. 346, 1033-1039 (2006).
[22] Laemmli, U K. Cleavage of structural proteins during the assembly of the head of bacteriophage T4. Nature 227, 680-685 (1970).
[23] Mauch, C. et al. Regulation of collagen synthesis in fibroblasts within a three-dimensional collagen gel. Exp. Cell Res. 178, 493-503 (1988).
[24] Damour, O. et al. A dermal substrate made of collagen-GAG-chitosan for deep burn coverage: first clinical uses. Clin. Mater. 15, 273-276 (1994).
[25] Schlotmann, K. et al. Cosmetic efficacy claims in vitro using a three-dimensional human skin model. Int. J. Cosmet. Sci. 23, 309-318 (2001).
[26] Stuhlmann, D. et al. Paracrine effect of TGF-beta1 on downregulation of gap junctional intercellular communication between human dermal fibroblasts. Biochem. Biophys. Res. Commun. 319, 321-326 (2004).
[27] Heckert, E. G. et al. Fenton-like reaction catalyzed by rare earth inner transition metal cerium. Environ. Sci. Technol. 42, 5014-5019 (2008).
[28] Rzigalinski, B. A. et al. Radical nanomedicine. Nanomedicine 1, 399-412 (2006).
[29] Chen, J. et al. Rare earth nanoparticles prevent retinal degeneration induced by intracellular peroxides. Nat. Nanotechnol. 1:142-150 (2006)
[30] Schubert, D. et al. Cerium and yttrium oxide nanoparticles are neuroprotective. Biochem. Biophys. Res. Commun. 342, 86-91 (2006).
[31] Tarnuzzer, R. W. et al. Vacancy Engineered Ceria Nanostructures for Protection from Radiation-Induced Cellular Damage. Nano Lett. 5, 2573-2577 (2005).
[32] Treiber, N. et al. Overexpression of manganese superoxide dismutase in human dermal fibroblasts enhances the contraction of free floating collagen lattice: implications for ageing and hyperplastic scar formation. Arch. Dermatol. Res. 301, 273-287 (2009)
[33] Kessler, D. et al. Fibroblasts in mechanically stressed collagen lattices assume a "synthetic" phenotype. J. Biol. Chem. 276, 36575-36585 (2001).
[34] Arora, P. D. McCulloch, C. A. Dependence of collagen remodelling on alpha-smooth muscle actin expression by fibroblasts. J. Cell. Physiol. 159, 161-175 (1994).
[35] Ljinen, P. et al. Transforming growth factor-beta 1 promotes contraction of collagen gel by cardiac fibroblasts through their differentiation into myofibroblats. Methods Find. Exp. Clin. Pharmacol. 25, 79-86 (2003).
[36] Levine, R. L. et al. Carbonyl assays for determination of oxidatively modified proteins. Methods Enzymol. 233, 346-357 (1994).
[37] de Wever, O. Mareel, M. Role of myofibroblasts at the invasion front. Biol. Chem. 383, 55-67 (2002).
[38] Nadege, D. et al. Mitochondria: from bioenergetics to the metabolic regulation of carcinogenesis. Front. Biosci. 14, 4015-4034 (2009).
[39] Moller, P. et al. Role of oxidative damage in toxicity of particulates. Free Radic. Res. 44, 1-46 (2010).
[40] Oberdörster, G. et al. Nanotoxicology: an emerging discipline evolving from studies of ultrafine particles. Environ. Health Perspect. 113, 823-829 (2005).

[41] Shvedova, A. A. et al. Exposure to carbon nanotube material: assessment of nanotube cytotoxicity using human keratinocyte cells. J. Toxicol. Environ. Health A 66, 1909-1926 (2003).
[42] Warheit, D. B. Nanoparticles: Health impacts ? Mater. Today 7, 32-35 (2004)
[43] Heckert, E. et al. The role of cerium redox state in the SOD mimetic activity of nanoceria. Biomaterials 29, 2705-2709 (2008).
[44] Auffan, M. et al. CeO2 nanoparticles induce DNA damage towards human dermal fibroblasts in vitro. Nanotoxicol. 3, 161-171 (2009).
[45] Korsvik, C. et al. Superoxide dismutase mimetic properties exhibited by vacancy engineered ceria nanoparticles. Chem. Commun. 14, 1056-1058 (2007).
[46] Perez, J. M. et al. Synthesis of biocompatible dextran-coated nanoceria with pH-dependent antioxidant properties. ASMAll 4, 552-556 (2008).
[47] Ristow, M. Oxidative metabolism in cancer growth. Curr. Opin. Clin. Nutr. Metab. Care. 9, 339-345 (2006).
[48] Warburg, O. On the origin of cancer cells. Science 123, 309-314 (1956).
[49] Zhivotovsky, B. Orrenius, S. The Warburg effect returns to the cancer stage. Sem. Cancer Biol. 19, 1-3 (2009).
[50] Semenza, G. L. Tumor metabolism: cancer cells give and take lactate. J. Clin. Invest. 118, 3835-3837 (2008).

That which is claimed is:

1. A method of promoting a cytotoxic anti-invasive effect on squamous tumor cells having an acidic internal cell environment, the method comprising contacting the cells with a nanoparticle composition comprising a cerium oxide core coated with dextran, wherein $Ce^{4+}$ is in higher concentration than $Ce^{3+}$ in the composition as measured by an absorption edge which lies beyond 350 nm, and wherein the nanoparticles have a diameter of approximately 3 to 5 nm, wherein the concentration of the nanoparticles in contact with the tumor cells is from 100 to 300 micromolar.

2. A method of inhibiting tumor invasiveness, the method comprising contacting tumor cells with a composition of dextran coated cerium oxide nanoparticles containing a predominance of $Ce^{4+}$ over $Ce^{3+}$ as measured by an absorption edge which lies beyond 350 nm, wherein the tumor cells are squamous cell skin cancer, wherein the concentration of the nanoparticles in contact with the tumor cells is from 100 to 300 micromolar.

3. The method of claim 2, wherein the nanoparticles have a diameter of approximately 3 to 5 nanometers.

4. A method of reducing tumor invasiveness of a squamous cell tumor, the method comprising contacting fibroblasts in the tumor's stroma with a composition of dextran-coated cerium oxide nanoparticles having a predominance of $Ce^{4+}$ over $Ce^{3+}$ as measured by an absorption

SEQUENCE LISTING

```
<160> NUMBER OF SEQ ID NOS: 4

<210> SEQ ID NO 1
<211> LENGTH: 20
<212> TYPE: DNA
<213> ORGANISM: Human

<400> SEQUENCE: 1
ctgttccagc catccttcat                                                   20

<210> SEQ ID NO 2
<211> LENGTH: 25
<212> TYPE: DNA
<213> ORGANISM: Human

<400> SEQUENCE: 2
tcatgatgct gctgttgtag gtggt                                             25

<210> SEQ ID NO 3
<211> LENGTH: 23
<212> TYPE: DNA
<213> ORGANISM: Human

<400> SEQUENCE: 3
attctttgct gacctgctgg att                                               23

<210> SEQ ID NO 4
<211> LENGTH: 24
<212> TYPE: DNA
<213> ORGANISM: Human

<400> SEQUENCE: 4
cttaggcttt gtattttgct tttc                                              24
``` edge which lies beyond 350 nm, wherein the concentration of the nanoparticles in contact with the tumor cells is from 100 to 300 micromolar.

5. The method of claim 4, wherein the wherein the nanoparticles have a diameter of approximately 3 to 5 nanometers.

6. The method of claim 4, wherein the nanoparticles are toxic to squamous cell tumor cells and non-toxic to normal cells.

7. The method of claim 4, wherein the method inhibits the transition of fibroblasts to myofibroblasts.

\* \* \* \* \*